US012303536B2

(12) United States Patent
Itescu et al.

(10) Patent No.: US 12,303,536 B2
(45) Date of Patent: *May 20, 2025

(54) METHOD FOR TREATING HEART FAILURE

(71) Applicant: Mesoblast International Sarl, Meyrin (CH)

(72) Inventors: Silviu Itescu, Melbourne (AU); Lee Golden, New York, NY (US)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,877

(22) Filed: May 17, 2023

(65) Prior Publication Data
US 2023/0364149 A1 Nov. 16, 2023

Related U.S. Application Data

(63) Continuation of application No. 15/534,371, filed as application No. PCT/EP2015/081042 on Dec. 22, 2015, now Pat. No. 11,712,452.

(30) Foreign Application Priority Data

Dec. 23, 2014 (AU) .................. 2014905243

(51) Int. Cl.
*A61K 35/28* (2015.01)
(52) U.S. Cl.
CPC .................. *A61K 35/28* (2013.01)
(58) Field of Classification Search
None
See application file for complete search history.

(56) References Cited

U.S. PATENT DOCUMENTS

2017/0333482 A1    11/2017    Itescu et al.

FOREIGN PATENT DOCUMENTS

| WO | WO 99/03973 A1 | 1/1999 |
| WO | WO 2012/027740 A1 | 3/2012 |
| WO | WO 2014/057097 A1 | 4/2014 |

OTHER PUBLICATIONS

Torabi, A. et al. 2014. Development and course of heart failure after a myocardial infarction in younger and older people. Journal of Geriatric Cardiology 11: 1-12; specif. p. 1 (Year: 2014).*
Hare, J.M. et al. 2009. A randomized, double-blind, placebo-controlled, dose-escalation study of intravenous adult human mesenchymal stem cells (Prochymal) after acute myocardial infarction. Journal of the American College of Cardiology 54(24): 2277-2286; specif. pp. 2277, 2278, 2283, 2284 (Year: 2009).*
Alvarez-Viejo, M. et al. 2013. Quantifying mesenchymal stem cells in the mononuclear cell fraction of bone marrow samples obtained for cell therapy. Transplantation Proceedings 45: 434-439; specif. pp. 434, 435 (Year: 2013).*
Suarez de Lezo, J. et al. 2007. Regenerative therapy in patients with a revascularized acute anterior myocardial infarction and depressed ventricular function. Revista Espanola de Cardiologia 60(4): 357-365; specif. pp. 357, 358, 360, 361 (Year: 2007).*
Meluzin, J. et al. 2006. Autologous transplantation of mononuclear bone marrow cells in patients with acute myocardial infarction: The effect of the dose of transplanted cells on myocardial infarction. American Heart Journal 152: 975.e9-975.e15; specif. pp. 975. e9, 975.e10, 975.e11, 975.e12 (Year: 2006).*
Mazo, M. et al. 2010. Transplantation of mesenchymal stem cells exerts a greater long-term effect than bone marrow mononuclear cells in a chronic myocardial infarction model in rat. Cell Transplantation 19: 313-328; specif. p. 313 (Year: 2010).*
Psaltis, P.J. et al. 2010. Enrichment for STRO-1 expression enhances the cardiovascular paracrine activity of human bone marrow-derived mesenchymal cell populations. Journal of Cellular Physiology 223: 530-540; specif. pp. 530, 531, 538 (Year: 2010).*
Bernstein, H.S. et al. 2012. Stem cell therapy for cardiac disease. Pediatric Research 71(4): 491-499; specif. p. 491 (Year: 2012).*
Joshua M. Hare, et al., "Comparison of Allogenic vs Autologous Bone Marrow-Derived Mesenchymal Stem Cells Delivered by Transendocardio Injection in Patients with Ischemic Cardiomyopathy", JAMA: The Journal of the American Medical Association, Dec. 12, 2012, vol. 308, No. 22, pp. 2369.
Liu Bei, et al., "Effectiveness and safety of selected bone marrow stem cells on left ventricular function in patients with acute myocardial infarction: A meta-analysis of randomized controlled trials", International Journal of Cardiology, Nov. 4, 2014, vol. 177, No. 3, pp. 764-770.
Henning, R. J., "Stem cells in cardiac repair", Future Cardiology, Jan. 2011, vol. 7, No. 1, pp. 99-117, Future Medicine Ltd., GBR.
Jun-Won Lee, et al., "A Randomized, Open-Label, Multicenter Trial for the Safety and Efficacy of Adult Mesenchymal Stem Cells after Acute Myocardial Infarction", Journal of Korean Medical Science, Jan. 2014, vol. 29, No. 1, pp. 23, Seoul, KR.
McManus D. D., et al., "Prognostic Value of Left Centricular End-Systolic Volume Index as a Predictor of Heart Failure Hospitalization in Stable Coronary Artery Disease: Data from the Heart and Soul Study", Journal of the American Society of Echocardiograph, Feb. 2009, vol. 22, No. 2, pp. 190-197, Mosby-Year Book, Inc., Sy. Louis, MC, US.
International Search Report in connection with PCT International Application No. PCT/EP2015/081042, 2016.
Written Opinion of the International Searching Authority in connection with PCT International Application No. PCT/EP2015/081042, 2016.
Written Opinion issued Mar. 15, 2018 by the Intellectual Property Office of Singapore in connection with related Singaporean Patent Application No. 11201704780U.

(Continued)

*Primary Examiner* — Adam Weidner
*Assistant Examiner* — Sharon M. Papciak
(74) *Attorney, Agent, or Firm* — John P. White

(57) ABSTRACT

Methods for treating chronic heart failure due to left ventricular end systolic (LVESV) dysfunction with STRO-1+ mesenchymal linage precursor cells (MPCs) are provided.

14 Claims, 15 Drawing Sheets

(56) References Cited

OTHER PUBLICATIONS

W.A. Noort et al., "Human versus porcine mesenchymal stromal cells: phenotype, differentiation potential, immunomodulation and cardiac improvement after transplantation", J. Cell. Mol. Med., 2012, vol. 16, No. 8, pp. 1827-1839.
English Translation of Office Action issued Feb. 11, 2023 in connection with corresponding Korean Patent Application No. KR 10-2017-7018961.
Strauer, B et al., "Repair of Infarcted Myocardium by Autologous Intracoronary Mononuclear Bone Marrow Cell Transplantation in Humans", Circulation, 106: 1913-1918, Oct. 8, 2022.
U.S. Patent Application Publication No. US 2017/0333482 A1, published Nov. 23, 2017, in the name of Mesoblast International Sàrl.
PCT International Application Publication No. WO 2012/027740 A1, published Mar. 1, 2012, in the name of University of Miami et al.
PCT International Application Publication No. WO 2014/057097 A1, published Apr. 17, 2014, in the name of Institute National de la Sante et de la Recherche Medicale.
PCT International Application Publication No. WO 99/03973 A1, published Jan. 28, 1999, in the name of Osiris Therapeutics, Inc., et al.
International Search in connection PCT Report with International Application No. PCT/EP2015/081042.
Written Opinion of the International Searching Authority in connection with PCT International Application No. PCT/EP2015/081042.

\* cited by examiner

METHOD FOR TREATING HEART FAILURE

CROSS-REFERENCE TO RELATED APPLICATIONS

This application is a continuation of U.S. application Ser. No. 15/534,371, filed Jun. 8, 2017, now allowed, which is a § 371 national stage of PCT International Application No. PCT/EP2015/081042, filed Dec. 22, 2015, claiming priority to Australian Patent Application No. 2014905243, filed Dec. 23, 2015, the entire contents of each of which are hereby incorporated by reference in their entirety.

FIELD OF THE DISCLOSURE

The present disclosure relates to methods for treating or preventing heart failure in subjects with elevated left ventricular end systolic volume (LVESV).

BACKGROUND

Heart failure due to myocardial infarction (MI) is still one of the main causes of mortality and morbidity in developed countries. A recent update of US Medicare records was published that evaluated data involving 350,509 acute MI hospitalization in patients>65 years who were discharged alive after their event (Schuster et al. (2004) Physiol Heart Circa Physiol., 287(2):525-32). Within the first year post the index event, 25.9% of the MI patients died with 50.5% re-hospitalized. In the month after a MI, the likelihood of death was 21 times higher and the likelihood of hospitalization was 12 times higher than among the general Medicare-age population.

Patients who have larger Infarcts post MI and more post-infarct LV dysfunction are at significantly increased risk of experiencing mid-to-long term cardiac events and death. Specifically, anterior wall infarcts, larger infarcts, and more LV dysfunction in the post-infarct period are at significantly increased risk of experiencing mid-to-long term cardiac events and death (Eitel et al. (2010) J Am Coll Cardiol., 55:2470-9).

There is strong need in the art for new and effective methods for the prevention and treatment of heart failure, in particular treatment methods that avoid the need for heart transplant where the availability of organs is rare. In particular systems that allow heart tissue damage to be reversed or heart tissue defect to be repaired without presenting the risks and potential complications associated with general anesthesia and open heart surgery.

SUMMARY OF THE DISCLOSURE

Preclinical cardiac studies performed with mesenchymal lineage precursor cells have demonstrated unexpectedly that optimal results are generated in the setting of the greatest amount of myocardial damage. This raises the possibility that signals from damaged myocardium are necessary for "cross-talk" at the tissue level between the underlying biochemical/physiological derangements and the mesenchymal lineage precursor cells in order for the mesenchymal lineage precursor cells to release their "payload", namely paracrine factors. This observation has been supported by studies demonstrating that there are no significant mesenchymal lineage precursor cell-mediated effects when the cells are Injected into healthy myocardial tissue.

The present disclosure is based upon the observation that myocardial administration of mesenchymal precursor cells (MPCs) In patients with advanced chronic heart failure due to significant left ventricular contractile abnormalities (i.e. systolic dysfunction) enhance the efficacy signals of the MPCs. In particular, the present disclosure Is based upon the finding that subjects with moderately severe left ventricular contractile damage respond well to transendocardial delivery of MPCs and that the greater the magnitude of baseline left ventricular contractile abnormality in patients with chronic heart failure due to left ventricular systolic dysfunction, the more beneficial the MPC-related cardioprotective effect.

More particularly, the Inventors have found that the use of a baseline left ventricular end-systolic volume (LVESV) cut-off in heart failure subjects, identifies a subject population with advanced heart failure at high risk for a major adverse cardiac event (MACE) and identifies a subject population that responds optimally to administration of MPCs.

The present disclosure provides a method for treating or preventing heart failure in a subject, comprising administering to a subject with an elevated left ventricular end systolic volume (LVESV) of greater than 70 mL, a population of mesenchymal lineage stem or precursor cells and/or progeny thereof and/or soluble factors derived therefrom.

In one example, the elevated LVESV is due to acute myocardial infarction. In another example, the elevated LVESV is due to chronic congestive heart failure.

In another example, the method comprises the steps of:
i) selecting a subject having an elevated LVESV of greater than 70 mL, and
ii) administering to the subject a population of mesenchymal lineage stem or precursor cells and/or progeny thereof and/or soluble factors derived therefrom.

In another example, the method comprises the steps of:
i) diagnosing a subject(s) with heart failure;
ii) selecting for a cohort of the diagnosed subjects having an elevated LVESV of greater than 70 mL; and
iii) administering to the subject(s) a population of mesenchymal lineage stem or precursor cells and/or progeny thereof and/or soluble factors derived therefrom.

In one example, the LVESV is greater than 80 mL, greater than 90 mL, greater than 100 mL, greater than 100 mL, greater than 110 mL, greater than 120 mL, or greater than 130 mL. In another example, the LVESV is greater than 80 mL/m$^2$, greater than 90 mL/m$^2$, greater than 100 mL/m$^2$, greater than 110 mL/m$^2$, greater than 120 mL/m, or greater than 130 mL/m$^2$.

In one example, the cells, progeny thereof or soluble factors are administered to the subject by a catheter-based system. In a further example, the cells, and/or progeny thereof and/or soluble factors are administered to the subject's myocardium at or near the site of tissue damage using a catheter inserted into the subject's venous system. In another example, the cells, and/or progeny thereof and/or soluble factors may be administered systemically. The delivery of cells, and/or progeny thereof and/or soluble factors may be performed after Identifying a region of the myocardium in need of treatment.

In a further example, the cells, and/or progeny thereof and/or soluble factors are administered to the subject by transendocardial Injection, intracoronary infusion or transepicardial injection.

In a further example, the subject is characterised as having a left ventricular ejection fraction (LVEF) of less than or equal to about 35%. In another example, the subject has an LVEF of less than about 35%, less than about 30%, less than about 25%, or less than about 20%.

In one example, the heart failure is due to hypertension, cardiomyopathy (ischemic or non-ischemic), myocarditis, obesity, or diabetes. In a further example, the mesenchymal lineage stem or precursor cells and/or progeny thereof and/or soluble factors derived therefrom are administered to the subject following diagnosis of heart failure.

In one example the subject has acute cardiomyopathy. In a further example, the subject has ischemic cardiomyopathy. In a further example, the subject has non-ischemic cardiomyopathy. In a further example, the subject has dilated or congestive cardiomyopathy. In a further example, the subject has restrictive cardiomyopathy.

In another example, the mesenchymal lineage stem or precursor cells and/or progeny thereof and/or soluble factors derived therefrom are administered to the subject following acute myocardial infarction. In a further example, the mesenchymal lineage stem or precursor cells and/or progeny thereof and/or soluble factors derived therefrom are administered to the subject between about 1 and 7 days following diagnosis of heart failure. In a further example, the mesenchymal lineage stem or precursor cells and/or progeny thereof and/or soluble factors derived therefrom are administered to the subject between about 1 and 7 days following myocardial infarction. In a further example, the mesenchymal lineage stem or precursor cells and/or progeny thereof and/or soluble factors derived therefrom are administered to the subject between about 3 and 5 days following diagnosis or heart failure, or following myocardial infarction.

In another example, the subject has a left ventricle Infarct size of between about 5% and 30%, or between about 10% and 20%.

Methods for diagnosing heart failure will be familiar to persons skilled in the art. Examples include physical examination of the subject, electrocardiogram, chest x-ray, determination of BNP and/or troponin level by blood test, echocardiography, Doppler ultrasound, holster monitor, nuclear heart scan, cardiac catheterization, stress test or cardiac magnetic resonance imaging (cardiac MRI).

Methods for selecting a subject having an elevated LVESV of greater than 70 mL according to the present disclosure will be familiar to persons skilled in the art. For example, the LVESV of the subject can be measured by apparatus known in the art, including, but not limited to two-dimensional echocardiography, magnetic resonance tomography, cardiac computed tomography (CT) or biplane left cineventriculography. Additionally, persons skilled in the art will be familiar with the metes and bounds of the term "elevated LVESV" as this term is understood in the art and as described elsewhere herein.

Administration of the mesenchymal lineage stem or precursor cells and/or progeny thereof according to the present disclosure may be performed on a subject receiving medication or other treatment for heart failure and/or Its symptoms. Alternatively, it may be performed on a subject that is not receiving any other medication or treatment for heart failure. In some examples, administration of mesenchymal lineage stem or precursor cells and/or progeny thereof according to the present disclosure is performed on a subject that has previously undergone coronary artery bypass grafting (CABG) or left ventricular assist device (LVAD) implantation. The CABG or LVAD implantation procedure undergone by the subject may or may not have been accompanied by simultaneous administration of the mesenchymal lineage stem or precursor cells and/or progeny thereof according to the present disclosure. In some examples, administration of the mesenchymal lineage stem or precursor cells and/or progeny thereof according to the present disclosure is performed on an individual that is undergoing CABG or LVAD implantation. In other examples, administration of the mesenchymal lineage stem or precursor cells and/or progeny thereof according to the present disclosure is performed on a subject that has not received and/or will not be receiving any therapy for treating damaged/defective heart tissue.

The present disclosure also provides a method for treating or preventing heart failure in a heart having an elevated LVESV of greater than 70 mL, comprising administering to the heart, a population of mesenchymal lineage stem or precursor cells and/or progeny thereof and/or soluble factors derived therefrom.

In one example, the LVESV is greater than 80 mL, greater than 90 mL, greater than 100 mL, greater than 100 mL, greater than 110 mL or greater than 120 mL. In another example, the LVESV is greater than 80 mL/m$^2$, greater than 90 mL/m$^2$, greater than 100 mL/m$^2$, greater than 110 mL/m$^2$, or greater than 120 mL/m$^2$.

In another example, the present disclosure provides a method for reducing elevated left ventricular end systolic volume (LVESV) in a heart having an LVESV of greater than 70 mL, comprising administering to the heart, a population of mesenchymal lineage stem or precursor cells and/or progeny thereof and/or soluble factors derived therefrom.

In one example, the LVESV Is greater than 80 mL, greater than 90 mL, greater than 100 mL, greater than 100 mL, greater than 110 mL or greater than 120 mL. In another example, the LVESV is greater than 80 mL/m$^2$, greater than 90 mL/m$^2$, greater than 100 mL/m$^2$, greater than 110 mL/m$^2$, or greater than 120 mL/m$^2$.

In another example, the reduction in LVESV is at least 20%, at least 15%, at least 10%, at least 5%, or at least 2% compared to the same heart which has not been administered mesenchymal lineage stem or precursor cells and/or progeny thereof and/or soluble factors derived therefrom.

In another example, the LVESV Is measured at about 6 months, at about 12 months, at about 24 months, or at about 36 months following administration of mesenchymal lineage stem or precursor cells and/or progeny thereof and/or soluble factors derived therefrom.

In one example, the cells, and/or progeny thereof and/or soluble factors are administered to the heart by a catheter-based system. In a further example, the cells, and/or progeny thereof and/or soluble factors are administered to the myocardium at or near the site of tissue damage. The delivery of cells, and/or progeny thereof and/or soluble factors may be performed after Identifying a region of the myocardium in need of treatment.

In a further example, the cells, and/or progeny thereof and/or soluble factors are administered to the heart by transendocardial injection, intracoronary Infusion or transepicardial injection.

In a further example, the heart Is further characterised as having a left ventricular ejection fraction (LVEF) of less than about 55%. In a further example, the heart Is further characterised as having a left ventricular ejection fraction (LVEF) of less than or equal to about 35%. In another example, the heart has an LVEF of less than about 35%, less than about 30%, less than about 25%, or less than about 20%.

In one example, the elevated LVESV is due to acute myocardial infarction. In a further example, the elevated LVESV is due to chronic congestive heart failure.

In a further example, the mesenchymal lineage stem or precursor cells and/or progeny thereof and/or soluble factors derived therefrom are administered to the heart following diagnosis of heart failure. In another example, the mesenchymal lineage stem or precursor cells and/or progeny thereof and/or soluble factors derived therefrom are administered to the heart following acute myocardial infarction. In a further example, the mesenchymal lineage stem or precursor cells and/or progeny thereof and/or soluble factors derived therefrom are administered to the heart between about 1 and 7 days following diagnosis of heart failure. In a further example, the mesenchymal lineage stem or precursor cells and/or progeny thereof and/or soluble factors derived therefrom are administered to the heart between about 1 and 7 days following acute myocardial infarction. In a further example, the mesenchymal lineage stem or precursor cells and/or progeny thereof and/or soluble factors derived therefrom are administered to the heart between about 3 and 5 days following diagnosis of heart failure or following myocardial infarction.

In another example, the heart has a left ventricular infarct size of between about 10% and 35%, or between about 11-34%, about 12-33%, about 13-32%, about 14-31%, about 15-30%, about 16-29%, or about 17-28% of the left ventricle.

In some embodiments, the methods of the present disclosure also comprise administering to the heart or to the subject, a population of mesenchymal lineage stem or precursor cells enriched for STRO-1+ cells and/or progeny thereof and/or soluble factors derived therefrom. In another example, the methods of the present disclosure comprise administering to the heart or to the subject, a population of mesenchymal lineage stem or precursor cells enriched for STRO-1$^{bright}$ cells and/or progeny thereof and/or soluble factors derived therefrom.

In another example, the population of mesenchymal lineage stem or precursor cells express tissue non-specific alkaline phosphatase (TNAP), and/or the progeny cells and/or soluble factors are derived from mesenchymal lineage cells that express TNAP. In another example, the population of mesenchymal lineage stem or precursor cells express angiopoietin-1 (Ang1) in an amount of at least 0.1 µg/$10^6$ cells and/or the progeny cells and/or soluble factors are derived from mesenchymal lineage precursor cells that express Ang1 in an amount of at least 0.1 µg/$10^6$ cells. In another example, the population of mesenchymal lineage stem or precursor cells express Ang1 in an amount of at least 0.5 µg/$10^6$ cells. In another example, the population of mesenchymal lineage stem or precursor cells express Ang1 in an amount of at least 1 µg/$10^6$ cells. In another example, the population of mesenchymal lineage stem or precursor cells express Vascular Endothelial Growth Factor (VEGF) in an amount less than about 0.05 µg/$10^6$ cells and/or the progeny cells and/or soluble factors are derived from mesenchymal lineage precursor cells that express VEGF in an amount less than about 0.05 µg/$10^6$ cells and/or the progeny cells. In another example, the population of mesenchymal lineage stem or precursor cells express VEGF in an amount less than about 0.03 µg/$10^6$ cells.

In another example, the population of mesenchymal lineage stem or precursor cells express Ang1:VEGF at a ratio of at least about 2:1 and/or the progeny cells and/or soluble factors are derived from mesenchymal lineage stem or precursor cells that express Ang1:VEGF at a ratio of at least about 2:1. In another example, the population of mesenchymal lineage stem or precursor cells express Ang1:VEGF at a ratio of at least about 10:1. In another example, the population of mesenchymal lineage stem or precursor cells express Ang1:VEGF at a ratio of at least about 20:1. In another example, the population of mesenchymal lineage stem or precursor cells express Ang1:VEGF at a ratio of at least about 30:1.

In one example, the population of mesenchymal lineage stem or precursor cells and/or progeny thereof are administered to the heart or to the subject in a therapeutically effective amount.

In one example, the population of mesenchymal lineage stem or precursor cells and/or progeny thereof are administered to the heart or to the subject over multiple doses. In a further example, the methods of the present disclosure comprise administering between $1 \times 10^6$ to $8 \times 10^8$ cells. In another example, the methods of the present disclosure comprise administering about $1.5 \times 10^6$ cells.

In one example, the mesenchymal lineage stem or precursor cells and/or progeny cells thereof and/or soluble factors derived therefrom are administered in the form of a composition comprising the mesenchymal lineage stem or precursor cells and/or progeny cells thereof and/or soluble factors derived therefrom together with a pharmaceutically acceptable carrier and/or excipient. In a further example, the population of mesenchymal lineage stem or precursor cells and/or progeny thereof have been expanded in culture prior to administration and/or prior to obtaining the soluble factors.

The present disclosure also provides use of a population of mesenchymal lineage stem or precursor cells and/or progeny thereof and/or soluble factors derived therefrom or a composition described herein for treating heart failure in a subject having an elevated LVESV of greater than 70 mL.

The present disclosure also provides use of a population of mesenchymal lineage stem or precursor cells and/or progeny thereof and/or soluble factors derived therefrom or a composition described herein for treating a heart having an elevated LVESV of greater than 70 mL.

In one example according to any use described herein, the elevated LVESV is due to acute myocardial infarction. In another example according to any use described herein, the elevated LVESV is due to chronic congestive heart failure.

The present disclosure also provides a population of mesenchymal lineage stem or precursor cells and/or progeny thereof and/or soluble factors derived therefrom in the manufacture of a medicament for treating heart failure in a subject having an elevated left ventricular end systolic volume (LVESV) of greater than 70 mL.

The present disclosure also provides a population of mesenchymal lineage stem or precursor cells and/or progeny thereof and/or soluble factors derived therefrom in the manufacture of a medicament for treating a heart having an elevated left ventricular end systolic volume (LVESV) of greater than 70 mL.

The present disclosure also provides a population of mesenchymal lineage stem or precursor cells and/or progeny thereof and/or soluble factors derived therefrom or a composition described herein for use in treating heart failure in a subject having an elevated LVESV of greater than 70 mL.

The present disclosure also provides a population of mesenchymal lineage stem or precursor cells and/or progeny thereof and/or soluble factors derived therefrom, or a composition described herein for use in treating a heart having an elevated left ventricular end systolic volume (LVESV) of greater than 70 mL.

In another example, the present disclosure provides use of a population of mesenchymal lineage stem or precursor cells and/or progeny thereof and/or soluble factors derived therefrom or a composition described herein for reducing the left ventricular end systolic volume (LVESV) in a heart having an elevated LVESV of greater than 70 mL.

In another example, the present disclosure provides a population of mesenchymal lineage stem or precursor cells and/or progeny thereof and/or soluble factors derived therefrom or a composition described herein for use in reducing the left ventricular end systolic volume (LVESV) In a heart having an elevated LVESV of greater than 70 mL.

In one example according to any population or use described herein, the LVESV is greater than 80 mL, greater than 90 mL, greater than 100 mL, greater than 110 mL or greater than 120 mL. In another example, the LVESV is greater than 80 mL/m$^2$, greater than 90 mL/m$^2$, greater than 100 mL/m$^2$, greater than 110 mL/m$^2$, or greater than 120 mL/m$^2$.

In a further example according to any method or use described herein, the population of mesenchymal lineage precursor cells and/or progeny thereof are isolated or purified.

In a further example, the population of mesenchymal lineage stem or precursor cells and/or progeny thereof are derived from a donor subject. The donor subject may be the same subject into which the cells, and/or progeny thereof and/or soluble factors derived therefrom are administered in which case the cells are autologous. In another example, the donor subject is a different subject Into which the cells, and/or progeny thereof and/or soluble factors derived therefrom are administered in which case the cells are allogeneic.

In a further example, the subject has a left ventricular ejection fraction (LVEF) of less than about 55%. In another example according to any use described herein, the subject has a LVEF of less than or equal to about 35%. In another example, the subject has an LVEF of less than about 35%, less than about 30%, less than about 25%, or less than about 20%.

In another example according to any use described herein, the heart has a left ventricular infarct size of between about 5% and 30%, or between about 10% and 20%. In another example according to any use described herein, the subject has a left ventricular infarct size of between about 5% and 30%, or between about 10% and 20%.

In another example, the present disclosure provides population of mesenchymal stem or lineage precursor cells and/or progeny thereof and/or soluble factors derived therefrom in the manufacture of a medicament for reducing the left ventricular end systolic volume (LVESV) in a heart having an elevated LVESV of greater than 70 mL.

The present disclosure also provides a kit comprising a population of mesenchymal lineage stem or precursor cells and/or progeny thereof and/or soluble factors derived therefrom or a composition described herein and a delivery device for administration of the cells, and/or progeny thereof and/or soluble factors. In one example, the delivery device is a catheter.

In another example, the subject according to the present disclosure is a mammal. In a further example, the subject is a human, including an adolescent human or pediatric human. In a particular example the subject is greater than or equal to 18 years of age.

In a further example, the subject has had a heart failure event in the twelve months preceding administration of the population of mesenchymal lineage stem or precursor cells and/or progeny thereof and/or soluble factors derived therefrom.

In a further example, the subject is classified as New York Heart Association (NYHA) class II, III or IV. Class II is defined as mild where subjects experience fatigue and shortness of breath during moderate physical activity. Class II is defined as moderate where patients experience shortness of breath during even light physical activity. Class IV or end-stage is defined as severe where patients are exhausted, even at rest.

In a further example, the subject has a decreased baseline six minute walk test (6MWT), meaning that the distance traversed by the subject over a six minute period is decreased relative to non heart-failure subjects.

In another example, the subject has a left ventricular end diastolic volume (LVEDS) of greater than 150 mL. In another example, the subject has a LVESV of greater than 170 mL.

In another example, the subject is also concomitantly administered conventional heart failure medication. In a further example, the heart failure medication includes, but is not limited to one or more of the following: beta blockers, ACE inhibitors or angiotension receptor blockers.

In another example, the subject has a high major adverse cardiac event (MACE) rate.

In a further example, the subject has a >50% heart failure-MACE (HF-MACE) rate over 36 months. In another example, the subject has a >60% HF-MACE rate, or >65% HF-MACE rate, or >70% HF-MACE rate over 36 months.

DESCRIPTION OF THE DRAWINGS

FIG. 3-1 shows baseline left ventricular end systolic volume (LVESV) values in placebo (control) and mesenchymal precursor cell (MPC) administered subjects (150 million cells) striated according to a LVESV of less than or equal to 100 mL or greater than 100 mL.

FIG. 3-2 shows the change in LVESV value at 6 months in placebo (control) and MPC administered subjects (150 million cells) striated according to a LVESV of less than or equal to 100 mL or greater than 100 mL.

FIG. 4-1 shows baseline left ventricular end diastolic volume (LVEDV) values in placebo (control) and MPC administered subjects (150 million cells) striated according to a LVESV of less than or equal to 100 mL or greater than 100 mL.

FIG. 4-2 shows the change in LVEDV value at 6 months in placebo (control) and MPC administered subjects (150 million cells) striated according to a LVESV of less than or equal to 100 mL or greater than 100 mL.

FIG. 6-1 shows baseline left ventricular ejection fraction (LVEF) values in placebo (control) and MPC administered subjects (150 million cells) striated according to a LVESV of less than or equal to 100 mL or greater than 100 mL.

FIG. 5-2 shows the change in LVEF value at 6 months in placebo (control) and MPC administered subjects (150 million cells) striated according to a LVESV of less than or equal to 100 mL or greater than 100 mL.

FIG. 6 shows the change in LVESV value at 6 months in placebo (control) and MPC administered subjects (150 million cells) striated according to a LVESV of greater than 70 mL.

DETAILED DESCRIPTION

Figure 1:
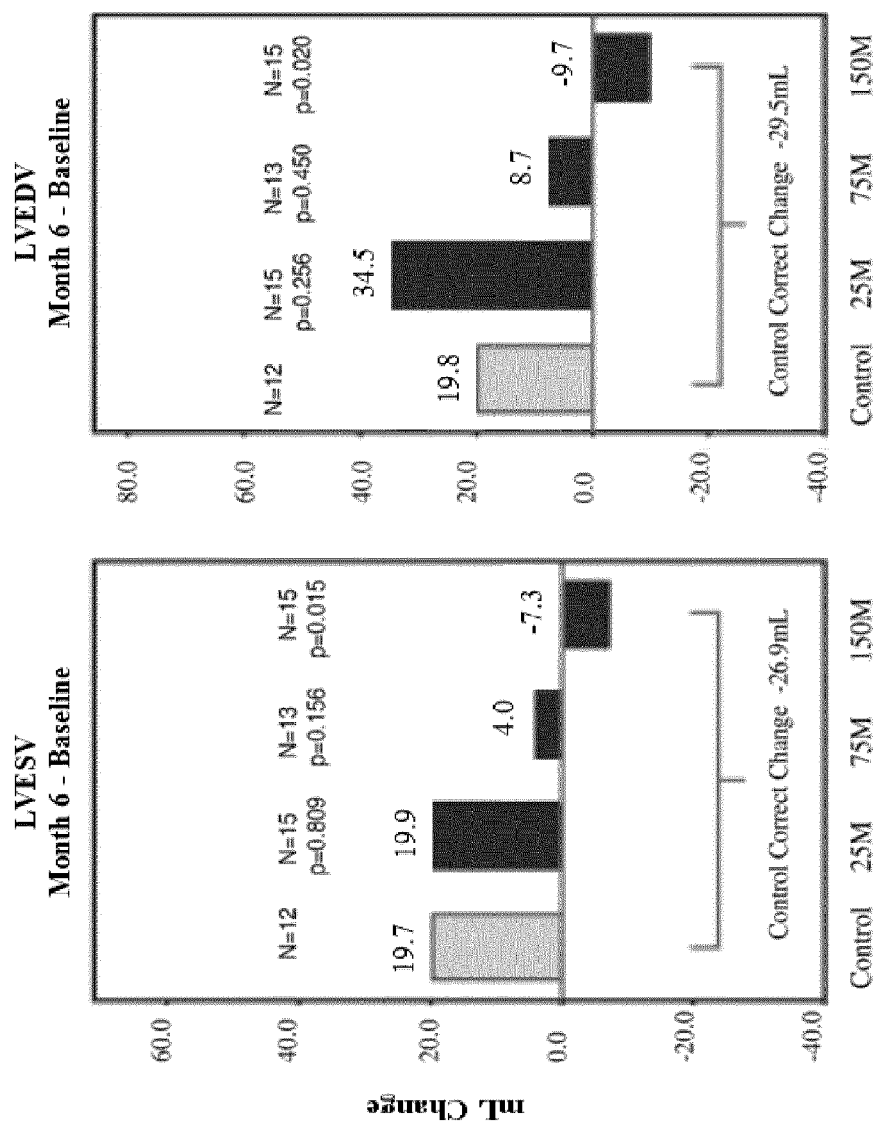
FIG. 1 shows dose dependent effect of MPC in cardiac remodelling based on left ventricular (LV) volumes.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the disclosure described herein is susceptible to variations and modifications other than those specifically described. It is to be understood that the disclosure Includes all such variations and modifications. The disclosure also includes all of the steps, features, compositions and compounds referred to or Indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

Unless specifically defined otherwise, all technical and scientific terms used herein shall be taken to have the same meaning as commonly understood by one of ordinary skill in the art (e.g., in cell culture, molecular genetics, stem cell differentiation, immunology, immunohistochemistry, protein chemistry, and biochemistry).

Unless otherwise Indicated, the surgical techniques utilized in the present disclosure are standard procedures, well known to those skilled in the art.

Methods of obtaining and enriching a population of mesenchymal lineage stem or precursor cells are known in the art. For example, enriched populations of mesenchymal lineage stem or precursor cells can be obtained by the use of flow cytometry and cell sorting procedures based on the use of cell surface markers that are expressed on mesenchymal lineage stem or precursor cells.

All documents cited or referenced herein, and all documents cited or referenced in herein cited documents, together with any manufacturer's Instructions, descriptions, product specifications, and product sheets for any products mentioned herein or in any document incorporated by reference herein, are hereby incorporated herein by reference in their entirety.

Selected Definitions

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the singular form "a", "an" and "the" include singular and plural references unless the context indicates otherwise.

As used herein, the term "heart failure" may be used interchangeably with the term "congestive heart failure (CHF)" and refers to a condition in which the heart cannot pump enough blood to the body's other organs due to, for example, heart muscle malfunction, weakening of the heart muscle, referred to as "cardiomyopathy" and other heart muscle related reasons. Congestive heart failure is characterised, among other effects, by left ventricle (LV) chamber dilation, decrease LV contractility and elevated levels of circulating catecholamines. In another example, heart failure occurs due to Ischemic and other reperfusion, and other non-ischemic factors. Heart failure includes, but is not limited to the following symptoms or signs individually or collectively: cardiac reperfusion injury, compensated hypertrophy, human end stage heart failure, hypertensive cardonyopathy, left ventricular hypertension, left or right ventricular dilation, left or right ventricular failure, maladaptive hypertrophy, myocardial structural disarrangement (apoptosis and loss of cardkornyocytes) and myocardial dysfunction (loss in contraction and/or relaxation) and pressure overloaded heart.

By "Isolated" or "purified" It is meant a cell which has been separated from at least some components of its natural environment. This term includes gross physical separation of the cells from its natural environment (e.g. removal from a donor). The term "isolated" includes alteration of the cell's relationship with the neighbouring cells with which it is in direct by, for example, dissociation. The term "Isolated" does not refer to a cell which is in a tissue section. When used to refer to the population of cells, the term "isolated" includes populations of cells which result from proliferation of the Isolated cells of the disclosure.

As used herein, the term "left ventricular hypertension (LVH)" is a condition wherein the cardiac muscle responds to Increased resistance in the circulation by becoming enlarged. However, with time, the fibers of the hypertrophied heart muscle become thickened and shortened and consequently less able to relax. Hypertension makes the myocardium work harder. The resulting hypertrophy is the product of the thickening or shortening of the muscle fibers of the heart. Under these conditions, it becomes more difficult for the heart to relax and go through the normal cycle of contraction and relaxation. Changes in the myocardium appear in the collagen resulting in Increased stiffness. The outcome of this process is a heart that is less able to meet the output demands of normal circulation.

As used herein, the term "left ventricular dilation" refers to a left ventricular enlargement, which can increase the volume of blood that is ejected from the ventricle, temporarily improving cardiac output. This increase in size of the ventricle cavity however also results in a reduction of the percentage of left ventricular volume of blood that is effected (called ejection fraction) and has significant physiological implications. Left ventricular dilation is a well-recognised precursor and sign of ventricular dysfunction and congestive heart failure after myocardial infarction. Similarly, right ventricular dilation refers to a right ventricular enlargement and associated signs or disorder.

As used herein, the term "left ventricular failure" refers to a disorder where the left side of the heart fails to pump blood effectively. This results in a back-flow, pressure and/or congestion of blood into the lungs. Signs Indicating left ventricular failure include a laterally displaced apex beat. A gallop rhythm may be heard as a marker of increased blood flow or increased intra-cardiac pressure.

As used herein, the term "cardiomyopathy" refers to a condition in which the heart muscle (the myocardium) becomes inflamed and enlarged. Several different types of cardiomyopathy are known in the art, including dilated cardiomyopathy in which the heart muscle is stretched and becomes thinner, hypertrophic cardiomyopathy in which the heart muscle cells enlarge and cause the walls of the heart to thicken, and restrictive cardiomyopathy in which the heart becomes stiff and rigid because of abnormal tissue e.g. scar tissue.

As used herein, the term "myocardial infarction" is also understood as referring to a heart attack. Heart attack occurs when blood stops flowing properly to a part of the heart and the heart muscle is Injured because it is not receiving enough oxygen. This can occur when one of the coronary arteries that supplies blood to the heart develops a blockage.

The term "left ventricular end systolic volume" (LVESV) as used herein refers to the volume of blood in the left ventricle at the end of contraction, or systole, and the beginning of filing or diastole. It refers to the lowest volume of blood in the ventricle at any point in the cardiac cycle. Normal values for males typically range from 22-58 mL and for females from 19-49 mL. By way of explanation, the LVESV value referred to herein is the baseline LVESV value, i.e. the LVESV value which is determined prior to administration of the mesenchymal lineage precursor or stem cells and/or progeny thereof and/or soluble factors derived therefrom to the subject.

The term "elevated LVESV" will be understood by persons skilled in the art. Typically, it is understood to mean a value which is above the normal LVESV range for a male or female. In one example, an elevated LVESV will be understood to mean a value greater than 70 mL. In another example, it is understood to mean a LVESV value greater than 100 ml.

The term "left ventricular end systolic volume index" (LVESVI) as used herein refers to the left ventricular end systolic volume indexed. The value is typically expressed as mL/m$^2$. The terms LVESV and LVESVI may be used interchangeably herein.

The term "left ventricular ejection fraction" (LVEF) as used herein refers to how well the heart pumps with each contraction. Ejection fraction (EF) is typically expressed as a percentage i.e. the percentage of blood leaving your heart each time it contracts. A normal LVEF ranges from 55-70%. An LVEF of 65% for example means that 65% of the total amount of blood in the left ventricle is pumped out with each heartbeat. Since the left ventricle is the hearts main pumping chamber, the EF is usually measured only in the left ventricle (LV). An LVEF of 55% or higher is considered normal. An LVEF of 50% or lower is considered reduced. Experts vary in their opinion about an EF between 50 and 55% and some consider this to be a borderline range.

The term "left ventricular end diastolic volume" (LVEDV) as used herein refers to the volume of blood in the right ventricle at the end of contraction, or systole, and the beginning of filling or diastole. It refers to the lowest volume of blood in the ventricle at any point in the cardiac cycle. Typically, the LVEDV is a normal, healthy subject is about 120 mL. By way of explanation, the LVEDV value referred to herein is the baseline LVEDV value, i.e. the LVEDV value which is determined prior to administration of the mesenchymal lineage precursor cells and/or progeny thereof and/or soluble factors derived therefrom to the subject.

As used herein, the terms "treating", "treat" or "treatment" include administering a population of mesenchymal lineage stem or precursor cells and/or progeny thereof and/or soluble factors derived therefrom to thereby reduce or eliminate at least one symptom of heart failure. In one particular example, the treatment reduces the LVESV value by at least 5%, at least 10%, at least 15%, at least 20%, at least 25%, at least 30%, at least 35%, at least 40%, at least 45%, or at least 50% compared to the baseline value (i.e. before administration of mesenchymal lineage stem or precursor cells and/or progeny thereof and/or soluble factors derived therefrom).

The term "prevent" or "preventing" as used herein include administering a population of mesenchymal lineage stem or precursor cells and/or progeny thereof and/or soluble factors derived therefrom to thereby stop or hinder the development of at least one symptom of heart failure.

The term "subject" as used herein refers to a mammal, including but not limited to murines, rats, simians, humans, domestic and farm animals.

Mesenchymal Lineage Precursor Cells

As used herein, the term "mesenchymal lineage precursor or stem cell" refers to undifferentiated multipotent cells that have the capacity to self renew while maintaining multipotency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells. For the avoidance of doubt, a "mesenchymal lineage precursor cell" refers to a cell which can differentiate into a mesenchymal cell such as bone, cartilage, muscle and fat cells, and fibrous connective tissue.

The term "mesenchymal lineage precursor or stem cells" includes both parent cells and their undifferentiated progeny. The term also includes mesenchymal precursor cells, multipotent stromal cells, mesenchymal stem cells (MSCs), perivascular mesenchymal precursor cells, and their undifferentiated progeny.

Mesenchymal lineage precursor or stem cells can be autologous, xenogenic, syngenic or Isogenic. Autologous cells are Isolated from the same individual to which they will be reimplanted. Allogeneic cells are Isolated from a donor of the same species. Xenogenic cells are isolated from a donor of another species. Syngenic or isogenic cells are isolated from genetically identical organisms, such as twins, clones, or highly inbred research animal models. Mesenchymal lineage precursor or stem cells reside primarily in the bone marrow, but have also shown to be present in diverse host tissues including, for example, cord blood and umbilical cord, adult peripheral blood, adipose tissue, trabecular bone and dental pulp.

In one example the mesenchymal lineage precursor cells are STRO-1+ mesenchymal precursor cells (MPCs). As used herein, the phrase "STRO-1+ multipotential cells" shall be taken to mean STRO-1+ and/or TNAP+ progenitor cells capable of forming multipotential cell colonies.

STRO-1+ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

Mesenchymal lineage precursor or stem cells can be isolated from host tissues and enriched for by selection of STRO-1+ cells. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in (Simmons & Torok-Storb, 1991).

The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, as described and/or exemplified herein, cells (e.g., mesenchymal precursor cells) expressing STRO-2 and/or STRO-3 (TNAP) and/or STRO-4 and/or VCAM-1 and/or CD146 and/or 3G5 also express STRO-1 (and can be STRO-1bright). Accordingly, an Indication that cells are STRO-1+ does not mean that the cells are selected solely by STRO-1 expression. In one example, the cells are selected based on at least STRO-3 expression, e.g., they are STRO-3+(TNAP+).

Reference to selection of a cell or population thereof does not necessarily require selection from a specific tissue source. As described herein STRO-1+ cells can be selected from or Isolated from or enriched from a large variety of sources. That said, in some examples, these terms provide support for selection from any tissue comprising STRO-1+ cells (e.g., mesenchymal precursor cells) or vascularized tissue or tissue comprising pericytes (e.g., STRO-1+ pericytes) or any one or more of the tissues recited herein.

In one example, the cells used in the present disclosure express one or more markers Individually or collectively selected from the group consisting of TNAP+, VCAM-1+, THY-1+, STRO-2+, STRO-4+ (HSP-900), CD45+, CD146+, 3G5+ or any combination thereof.

By "Individually" is meant that the disclosure encompasses the recited markers or groups of markers separately, and that, notwithstanding that Individual markers or groups of markers may not be separately listed herein the accompanying claims may define such marker or groups of markers separately and divisibly from each other.

By "collectively" is meant that the disclosure encompasses any number or combination of the recited markers or groups of markers, and that, notwithstanding that such numbers or combinations of markers or groups of markers may not be specifically listed herein the accompanying claims may define such combinations or sub-combinations separately and divisibly from any other combination of markers or groups of markers.

In one example, the STRO-1+ cells are STRO-1$^{bright}$ (syn. STRO-1$^{bri}$). In another example, the STRO-1$^{bri}$ cells are preferentially enriched relative to STRO-1$^{dim}$ or STRO-1$^{intermediate}$ cells.

In another example, the STRO-1$^{bri}$ cells are additionally one or more of TNAP+, VCAM-1+, THY-1+, STRO-2+, STRO-4+ (HSP-90p) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells (MPCs) are perivascular mesenchymal precursor cells as defined in WO 2004/85630, characterised by the presence of the perivascular marker 3G5. For example, the MPCs express a Marker of a perivascular cell, e.g., the cells are STRO-1+ or STRO-1$^{bri}$ and/or 3G5+. In one example, the cells are or were previously or are progeny of cells that were isolated from vascularized tissue or organs or parts thereof.

A cell that is referred to as being "positive" for a given marker may express either a low (lo or dim) or a high (bright, bri) level of that marker depending on the degree to which the marker is present on the cell surface, where the terms relate to intensity of fluorescence or other marker used in the sorting process of the cells. The distinction of 1o (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labelled or is undetectable above background levels, e.g., levels detected using an isotype control antibody.

The term "bright" or "bri" as used herein, refers to a marker on a cell surface that generates a relatively high signal when detectably labelled. Whilst not wishing to be limited by theory, it Is proposed that "bright" cells express more of the target marker protein (for example the antigen recognized by STRO-1) than other cells in the sample. For instance, STRO-1$^b$ cells produce a greater fluorescent signal, when labelled with a FITC-conjugated STRO-1 antibody as determined by fluorescence activated cell sorting (FACS) analysis, than non-bright cells (STRO-1dull/dim). In one example, "bright" cells constitute at least about 0.1% of the most brightly labeled bone marrow mononuclear cells contained in the starting sample. In other examples, "bright" cells constitute at least about 0.5%, at least about 1%, at least about 1.5%, or at least about 2%, of the most brightly labelled bone marrow mononuclear cells contained in the starting sample. In an example, STRO-1bright cells have 2 log magnitude higher expression of STRO-1 surface expression relative to "background", namely cells that are STRO-1⁻. By comparison, STRO-1dim and/or STRO-1intermediate cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ cells are capable of differentiation into at least two different germ lines. Non-limiting examples of the lineages to which the STRO-1+ cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive Insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In an example of the present disclosure, the mesenchymal lineage precursor or stem cells are mesenchymal stem cells (MSCs). The MSCs may be a homogeneous composition or may be a mixed cell population enriched in MSCs. Homogeneous MSC compositions may be obtained by culturing adherent marrow or periosteal cells, and the MSCs may be identified by specific cell surface markers which are Identified with unique monoclonal antibodies. A method for obtaining a cell population enriched in MSCs Is described, for example, in U.S. Pat. No. 5,486,359. Alternative sources for MSCs include, but are not limited to, blood, skin, cord blood, muscle, fat, bone, and perichondrium.

In another example, the mesenchymal lineage precursor or stem cells are CD29+, CD54+, CD73+, CD90+, CD102+, CD106+, CD166+, MHC1+ MSCs (e.g. remestemcel-L).

Isolated or enriched mesenchymal lineage precursor or stem cells can be expanded in vitro by culture. Isolated or enriched mesenchymal lineage precursor or stem cells can be cryopreserved, thawed and subsequently expanded in vitro by culture.

In one example, isolated or enriched mesenchymal lineage precursor or stem cells are seeded at 50,000 viable cells/cm² in culture medium (serum free or serum-supplemented), for example, alpha minimum essential media (αMEM) supplemented with 5% fetal bovine serum (FBS) and glutamine, and allowed to adhere to the culture vessel overnight at 37° C., 20% O₂.

The culture medium is subsequently replaced and/or altered as required and the cells cultured for a further 68 to 72 hours at 37° C., 5% O₂.

As will be appreciated by those of skill in the art, cultured mesenchymal lineage precursor or stem cells are phenotypically different to cells in vivo. For example, in one embodiment they express one or more of the following markers, CD44, NG2, DC146 and CD140b. Cultured mesenchymal lineage precursor or stem cells are also biologically different to cells in vivo, having a higher rate of proliferation compared to the largely non-cycling (quiescent) cells in vivo.

Mesenchymal lineage precursor or stem cells may also be cryopreserved prior to administration to a subject.

Modification of the Cells

In one example, mesenchymal lineage precursor or stem cells of the present disclosure may be genetically modified or genetically unmodified and express Ang1 in an amount of at least 0.1 μg/10⁶ cells. However, in various examples it is envisaged that the mesenchymal lineage stem or precursor cells of the present disclosure may express Ang1 in an amount of at least 0.2 μg/10⁶ cells, 0.3 μg/10⁶ cells, 0.4 μg/10 cells, 0.5 μg/10 cells, 0.6 μg/10⁶ cells, 0.7 μg/10 cells, 0.8 μg/10⁶ cells, 0.9 μg/10 cells, 1 μg/10⁶ cells, 1.1 μg/10 cells, 1.2 μg/10⁶ cells, 1.3 μg/10 cells, 1.4 μg/10⁶ cells, 1.5 μg/10⁶ cells.

In an example, the mesenchymal lineage precursor or stem cells of the present disclosure are genetically unmodified and express Ang1 in an amount of at least 0.1 μg/10⁶ cells. However, in various embodiments of this example, it is envisaged that the mesenchymal lineage precursor or stem cells may express Ang1 in an amount of at least 0.2 μg/10⁶ cells, 0.3 μg/10⁶ cells, 0.4 μg/10⁶ cells, 0.5 μg/10⁶ cells, 0.6 μg/10 cells, 0.7 μg/10⁶ cells, 0.8 μg/10 cells, 0.9 μg/10⁶ cells, 1 μg/10⁶ cells, 1.1 μg/10⁶ cells, 1.2 μg/10 cells, 1.3 μg/10⁶ cells, 1.4 μg/10⁶ cells, 1.5 μg/10⁶ cells.

In another aspect, the mesenchymal lineage precursor or stem cells of the present disclosure express VEGF in an amount less than about 0.05 μg/10⁶ cells. However, in various embodiments it is envisaged that the mesenchymal lineage stem or precursor cells of the present disclosure may express VEGF in an amount less than about 0.05 μg/10⁶ cells, 0.04 μg/10⁶ cells, 0.03 μg/10⁶ cells, 0.02 μg/10⁶ cells, 0.01 μg/10⁶ cells, 0.009 μg/10⁶ cells, 0.008 μg/10⁶ cells, 0.007 μg/10 cells, 0.006 μg/10⁶ cells, 0.005 μg/10⁶ cells, 0.004 μg/10⁶ cells, 0.003 μg/10⁶ cells, 0.002 μg/10⁶ cells, 0.001 μg/10⁶ cells.

In an example, the mesenchymal lineage precursor or stem cells of the present disclosure are genetically unmodified and express VEGF In an amount less than about 0.05 μg/10⁶ cells. However, in various embodiments of this example, it is envisaged that the mesenchymal lineage precursor or stem cells of the present disclosure may express VEGF in an amount less than about 0.05 μg/10⁶ cells, 0.04 μg/10⁶ cells, 0.03 μg/10⁶ cells, 0.02 μg/10⁶ cells, 0.01 μg/10⁶ cells, 0.009 μg/10⁶ cells, 0.008 μg/10⁶ cells, 0.007 μg/10⁶ cells, 0.008 µg/10$^6$ cells, 0.005 µg/10$^6$ cells, 0.004 µg/10$^6$ cells, 0.003 µg/10$^6$ cells, 0.002 µg/10$^6$ cells, 0.001 µg/10$^6$ cells.

The amount of cellular Ang1 and/or VEGF that Is expressed in a composition or culture of mesenchymal lineage precursor or stem cells may be determined by methods known to those skilled in the art. Such methods Include, but are not limited to, quantitative assays such as quantitative ELISA assays, for example or fluorescence-linked Immunosorbent assay (FLISA), Western blot, competition assay, radioimmunoassay, lateral flow immunoassay, flow-through immunoassay, electrochemiluminescent assay, nephelometric-based assays, turbidometric-based assay, fluorescence activated cell sorting (FACS)-based assays for detection of Ang-1 or VEGF In culture medium used to culture mesenchymal lineage precursor cells or stem cells, and surface plasmon resonance (SPR or Biacore).

It is to be understood, however, that the scope of the present disclosure is not to be limited to any particular method for determining the amount or level of Ang1 or VEGF expressed in the mesenchymal lineage precursor or stem cells of the present disclosure.

In one example the level of Ang1 or VEGF expressed by a composition or culture of mesenchymal lineage precursor or stem cells is determined by an ELISA assay. In such an assay, a cell lysate from a culture of mesenchymal lineage precursor or stem cells is added to a well of an ELISA plate. The well may be coated with a primary antibody, either a monoclonal or a polyclonal antibody(ies), against the Ang1 or VEGF. The well then Is washed, and then contacted with a secondary antibody, either a monoclonal or a polyclonal antibody(ies), against the primary antibody. The secondary antibody is conjugated to an appropriate enzyme, such as horseradish peroxidase, for example. The well then may be Incubated, and then is washed after the incubation period. The wells then are contacted with an appropriate substrate for the enzyme conjugated to the secondary antibody, such as one or more chromogens. Chromogens which may be employed Include, but are not limited to, hydrogen peroxide and tetramethylbenzidine. After the substrate(s) is (are) added, the well Is incubated for an appropriate period of time. Upon completion of the incubation, a "stop" solution Is added to the well in order to stop the reaction of the enzyme with the substrate(s). The optical density (OD) of the sample then is measured. The optical density of the sample is correlated to the optical densities of samples containing known amounts of Ang1 or VEGF in order to determine the amount of Ang1 or VEGF expressed by the culture of mesenchymal lineage precursor or stem cells being tested.

In another aspect, the mesenchymal lineage precursor or stem cells of the present disclosure express Ang1:VEGF at a ratio of at least about 2:1. However, in various embodiments it is envisaged that the mesenchymal lineage precursor or stem cells of the present disclosure may express Ang1:VEGF at a ratio of at least about 10:1, 15:1, 20:1, 21:1, 22:1, 23:1, 24:1, 25:1, 26:1, 27:1, 28:1, 29:1, 30:1, 31:1, 32:1.

In one example, the mesenchymal lineage precursor or stem cells of the present disclosure are genetically unmodified and express Ang1:VEGF at a ratio of at least about 2:1. However, in various embodiments it is envisaged that the mesenchymal lineage precursor or stem cells of the present disclosure may express Ang1:VEGF at a ratio of at least about 10:1, 15:1, 20:1, 21:1, 22:1, 23:1, 24:1, 25:1, 26:1, 27:1, 28:1, 29:1, 30:1, 31:1, 32:1.

Methods for determining the Ang1:VEGF expression ratio will be apparent to one of skill in the art. In an example of a method of determining a ratio of Ang 1 and VEGF expression, Ang1 and VEGF expression levels are quantitated via quantitative ELISA as discussed above. In such an example, after quantifying the levels of Ang1 and VEGF, a ratio based on the quantitated levels of Ang1 and VEGF could be represented as: (level of Ang1/level of VEGF)= Ang1:VEGF ratio.

The mesenchymal lineage precursor or stem cells of the present disclosure may be altered in such a way that upon administration, lysis of the cell is inhibited. Alteration of an antigen can induce immunological non-responsiveness or tolerance, thereby preventing the induction of the effector phases of an immune response (e.g., cytotoxic T cell generation, antibody production etc.) which are ultimately responsible for rejection of foreign cells in a normal immune response. Antigens that can be altered to achieve this goal include, for example, MHC class I antigens, MHC class II antigens, LFA-3 and ICAM-1.

In another example, the mesenchymal lineage precursor or stem cells may be genetically modified to express an gene product to be supplied to the subject receiving the transplantation. Examples of gene products that can be delivered to a subject via genetically modified mesenchymal lineage precursor cells include gene products that can prevent future cardiac disorders, such as growth factors which encourage blood vessels to invade the heart muscle (e.g. vascular endothelial growth factor (VEGF), fibroblast growth factor (FGF), transforming growth factor beta (TGF-β) and angiotensin).

The mesenchymal lineage precursor or stem cells may also be genetically modified to express proteins of importance for the differentiation and/or maintenance of striated skeletal muscle cells. Exemplary proteins include growth factors (TGF-0, insulin-like growth factor 1 (IGF-1), FGF), myogenic factors (e.g. myoD, myogenin, myogenic factor 5 (Myf5), myogenic regulatory factor (MRF)), transcription factors (e.g. GATA-4), cytokines (e.g. cardiotropin-1), members of the neuregulin family (e.g. neuregulin 1, 2 and 3) and homeobox genes (e.g. Csx, tinman and NKx family).

Heart Failure

Heart failure occurs when the heart is unable to pump sufficiently to maintain blood flow to meet the needs of the body. One cause of heart failure Is myocardial infarction (MI). A MI occurs when blood stops flowing properly to a part of the heart. The lack of blood supply results in a localized area of myocardial necrosis referred to as an Infarct or Infarction. The infarcted heart is unable to pump sufficiently to maintain blood flow to meet the needs of the body leading to heart failure. Post-MI, a series of compensatory mechanisms are initiated, serving to buffer the fall in cardiac output and assisting to maintain sufficient blood pressure to perfuse the vital organs. As a result, patients with heart failure may not progress for extended periods of time. However, the compensatory mechanisms eventually fail to compensate for the damaged heart, resulting in a progressive decline in cardiac output, termed "progressive heart failure".

A diagnosis of MI is created by Integrating the history of the presenting illness and physical examination with electrocardiogram finding and cardiac markers. A coronary angiogram can be performed which allows visualisation of narrowings or obstructions on the heart vessels. According to WHO criteria as revised in 2000 (Alpert J S, Thygesen K, Antman E, Bassand J P. (2000). "Myocardial infarction redefined—a consensus document of The Joint European Society of Cardiology/American College of Cardiology Committee for the redefinition of myocardial infarction". J Am Coll Cardiol 36 (3): 959-89), a cardiac troponin rise accompanied by either typical symptoms, pathological Q waves, ST elevation or depression or coronary intervention are diagnostic of MI.

For more than 70 years, the 12-lead electrocardiogram (ECG) has remained the standard for determining the presence and location of MIs. It is universally available, noninvasive, Inexpensive and easily repeatable. The quantitative Selvester QRS scoring system (Selvester R H et al. (1985) Arch Intern Med 145(10):1877-1881) which was designed from computer simulations, utilises the information on the ECG to estimate MI size. The Selvester scoring system is a 50 criteria 31 point QRS scoring system based on observations of Q- and R-wave durations and R/Q and R/S amplitude ratios in the standard 12-lead ECG.

Methods for determining infarct size, including, but not limited to, QRS scoring are familiar to persons skilled in the art.

Cardiac markers can also be measured to determine incidence of MI. Such markers include troponins T and I, creatinine kinase, myoglobin levels, natriuretic peptides (e.g. B-type natriuretic peptide), C-reactive protein (CRP), erythrocyte sedimentation rate (ESR), heart type fatty acid binding protein and copeptin, mid-regional pro-strial natriuretic peptide, ST2, C-terminal pro-endothelin 1, and mid-regional pro-adrenomedullin.

Troponin is a protein released from myocytes when Irreversible myocardial damage occurs. It is highly specific to cardiac tissue and accurately diagnoses myocardial infarction with a history of ischaemic pain or ECG changes reflecting ischaemia. Cardiac troponin level is dependent on infarct size, thus providing an indicator for the prognosis following an infarction.

The methods of the present disclosure relate to the treatment of the progressive decline in cardiac output characteristic of progressive heart failure.

Accordingly, "treat" and "treatment", in the context of the present disclosure refers to both therapeutic treatment and prophylactic or preventative measures.

In an example, treatment reduces the chance or risk of heart failure-related Major Adverse Cardiac Events (HF-MACE) defined as a composite of cardiac related death or resuscitated cardiac death, or non-fatal decompensated heart failure events. In an example, the chance of risk of HF-MACE is reduced over at least 6 months, at least 12 months, at least 24 months, at least 36 months.

In the context of the present disclosure it is envisaged that the terms chronic heart failure, congestive heart failure, congestive cardiac failure can be used interchangeably with "progressive heart failure".

Myocardial Infarction Induced Heart Failure

It Is generally known that patient prognosis and cardiac function are related to the amount of the left ventricle (LV) infarcted.

The term "myocardial infarction induced heart failure" refers to a subset of subjects in which myocardial infarction (MI) is the cause of heart failure. It is envisaged that the methods of the present disclosure can be used to treat progressive heart failure in a specific population of MI subjects.

In particular, the population of MI subjects are those having an LVESV of greater than 70 mL. In other examples, the LVESV is greater than 80 mL, greater than 90 mL, greater than 100 mL, greater than 110 mL, or greater than 120 mL. In one example, the subject has a proximal left anterior descending (LAD) arterial lesion. In the context of the present disclosure the term "arterial lesion" encompasses an obstructive lesion, occluding the LAD of the heart or an arterial lesion that previously occluded the LAD that has been treated, for example, via percutaneous coronary intervention (PCI), also known as angioplasty.

MI can cause persistent left ventricular dysfunction. Left ventricular dysfunction is characterised by a decrease in myocardial contractility. A reduction in the left ventricular ejection fraction (LVEF) results when myocardial contractility is decreased throughout the left ventricle. Thus, LVEF provides one way of determining left ventricular dysfunction. LVEF can be measured by a number of methods known in the art such as, but not limited to, two-dimensional echocardiography (ECG), magnetic resonance tomography, cardiac computed tomography (CT), radionuclide angiography, gated myocardial perfusion single-photon emission computed tomography (SPECT), gated myocardial perfusion positron emission tomography (PET) or biplane left cineventriculography.

LVEF can be measured using the following equation LVEF=stroke volume (EDV-ESV)/EDV. A change in LVEF of 5-10% is likely to represent a genuine fall in LVEF.

In an example, a subject with a LVEF of less than about 55% has left ventricular dysfunction. In other examples, a subject with a LVEF of less than about 54%, 53%, 52%, 51%, 50%, 49%, 48%, 47%, 46% has left ventricular dysfunction. In another example, a subject with a LVEF of less than about 45% has left ventricular dysfunction. In other examples, a subject with a LVEF of less than about 44%, 43%, 42%, 41% has left ventricular dysfunction. In another example, a subject with a LVEF of less than about 40% has left ventricular dysfunction. In other examples, a subject with a LVEF of less than about 39%, 38%, 37%, 36%, 35%, 34%, 33%, 32%, 31%, 30% has left ventricular dysfunction.

In the context of the present disclosure the term "persistent left ventricular dysfunction" is used to define left ventricular dysfunction that persists over a period of time or series of measurements. For example, "persistent left ventricular dysfunction" can include left ventricular dysfunction that persists for between about 1 to about 14 days post MI or longer. For example, persistent left ventricular dysfunction can include left ventricular dysfunction that persists for between about 1 to about 10, between about 1 to about 9, between about 2 to about 8, between about 2 to about 7 days post MI. In another example, "persistent left ventricular dysfunction" can include left ventricular dysfunction that persists across about 1 to 10 measurements or more.

The size or amount of myocardial necrosis post MI is referred to clinically as the infarct size. It is envisaged that the methods of the present disclosure relate to the treatment of MI subjects with large infarct size. For example, the subject treated using the methods of the present disclosure have an infarct size greater that about 10-35% of the left ventricle. In other examples, subjects have an infarct size greater that about 11-34%, about 12-33%, about 13-32%, about 14-31%, about 15-30%, about 16-29%, about 17-28% of the left ventricle. In another example, subjects have an infarct size greater that about 18.5% of the left ventricle. In other examples, subjects have an infarct size greater that about 19-27%, about 20-26%, about 21-25%, about 22-24%, about 23% of the left ventricle.

Infarct size can be measured via a number of methods known in the art. Examples, of such methods include the use of serum markers such as creatine kinase (CK), CK-MB, troponin I, and brain natriuretic peptide troponin.

In an example, subjects treated with the methods of the present disclosure have troponin levels at least about 2× the upper limits of normal (ULM).

In another example, subjects have troponin levels at least about 3×, about 4×, about 5×, about 6×ULM.

In an example, subjects treated with the methods of the present disclosure have creatine kinase-MB levels at least about 2× the upper limits of normal (ULM).

In another example, subjects have creatine kinase-MB levels at least about 3×, about 4×, about 5×, about 6×ULM.

Other examples of measuring infarct size include Sestamibi single-photon emission computed tomography (SPECT) myocardial perfusion imaging, magnetic resonance imaging. In one example, infarct size is measured using cardio magnetic resonance imaging (cMRI). Several cMRI techniques may be used for the diagnosis of infarct size. One of the most accurate and best validated techniques is delayed enhancement cardio magnetic resonance imaging (DE-CMR). In an example, cMRI Includes delayed-enhancement cardiac magnetic resonance imaging (DE-CMR).

When the appropriate settings for DE-CMR are used, normal myocardium appears black or nulled, whereas non-viable regions appear bright or hyperenhanced. Accordingly, in an example infarct size can be determined by visual assessment of the bright an hyper enhanced regions. Other examples of determining infarct size are known in the art (Slevers et al. (2007), Circulation, 115, 236-244; Kim et al. (2000), N Engl J Med, 343, 1445-1453). In brief, hyperenhancement is scored on a 17-segment model with a 5-point scale for each segment (0=no hyperenhancement, 1=1% to 25%, 2=26% to 50%, 3=51% to 75%, 4=76% to 100%). Dark regions entirely encompassed within hyperenhanced myocardium are interpreted as regions of microvascular damage (no-reflow) and included as part of the infarct. Infarct size as percent LV myocardium is calculated by summing the regional scores, each weighted by the hyperenhancement range midpoint (i.e., 1=13%, 2=38%, 3=63%, 4=88%) and dividing by 17. In another example, infarct size can be quantified by planimetry of hyperenhanced areas on the stack of short-axis images.

In an example, infarct size is measured between about 1 and 40 days post MI.

In other examples, Infarct size is measured between about 1 and 40 days, between about 2 and 35 days, between about 3 and 30 days, between about 4 and 25 days, between about 5 and 20 days, between about 6 and 15 days post MI.

In one example, infarct size is measured at about 30 days post MI.

In the context of the present disclosure "infarct size" refers to left ventricular Infarct size. Put another way, left ventricular infarct size refers to the amount of the left ventricle that is infarcted.

It is envisaged that the methods of the present disclosure can be used to treat progressive heart failure in a myocardial infarction subject with various stages or classifications of heart failure.

In one example, the heart failure staging is based on the American College of Cardiology (ACC) and the American Heart Association (AHA) staging criteria. In a further particular example, the subject has stage A. B, C or D heart failure according to the ACC or AHA criteria. In a still further example, the subject has stage B or C heart failure.

In another example, the heart failure classification is based on the New York Heart Association (NYHA) classification scale. In a further particular example, the subject has Class I, II, III or IV heart failure. In a still further example, the subject has stage II or Ill heart failure.

Catheter-Based Delivery Systems

Any catheter-based delivery system that allows for the injection of mesenchymal lineage precursor or stem cells and/or progeny thereof and/or soluble factor derived therefrom, or compositions comprising same into a subject's myocardium or at a site near the area of cardiac tissue damage can be used in the practice of the methods of the present disclosure. In certain examples, the catheter is Introduced percutaneously (e.g., into the femoral artery or another blood vessel) and routed through the vascular system to the subject's myocardium where it is used to deliver the mesenchymal lineage precursor or stem cells and/or progeny thereof and/or soluble factor derived therefrom, or compositions comprising same via a needle that is extruded from the end of the catheter. In other examples, the catheter reaches the heart through minimal surgical incision (e.g., limited thoracotomy, which Involves an Incision between the ribs).

Several catheters have been designed in order to precisely deliver agents to a damaged region within the heart, for example, an infarct region (see, for example, U.S. Pat. Nos. 6,102,926; 6,120,520; 6,251,104; 6,309,370; 6,432,119, and 6,485,481, each of which is incorporated herein by reference in its entirety). The catheter may be guided to the Indicated location by being passed down a steerable or guidable catheter having an accommodating lumen (see, for example, U.S. Pat. No. 5,030,204) or by means of a fixed configuration guide catheter (see, for example, U.S. Pat. No. 5,104, 393) Alternatively, the catheter may be advanced to the desired location within the heart by means of a deflectable stylet (see, for example WO 93/04724), or a deflectable guide wire (see, for example, U.S. Pat. No. 5,060,660).

The catheter may be coupled to a cardiac mapping system, which allows determination of the location and extent of the damaged/defective zone(s) (as described above). Once an area in need of treatment is Identified, the steering guide may be pulled out leaving the needle at the site of Injection. Part or all of the mesenchymal lineage precursor or stem cells and/or progeny thereof and/or soluble factor derived therefrom is sent down the lumen of the catheter and Injected into the myocardium. The catheter is retracted from the subject when all the Injections have been performed.

The needle element may be ordinarily retracted within a sheath at the time of guiding the catheter into the subject's heart to avoid damage to the venous system and/or the myocardium. At the time of injection, the needle is extruded from the tip of the catheter. During injection, the needle protrudes less than 10 mm, less than 7.5 mm or less than 5 mm into an adult heart muscle wall. Depending on the site of injection, the maximum length may be altered. For infants and children, the protrusion depth is correspondingly less, as determined by the actual or estimated wall thickness. The needle gauge used in transplantation of the cells can be, for example, 25 to 30.

In one example, the catheter used to deliver the mesenchymal lineage precursor or stem cells and/or progeny thereof and/or soluble factor derived therefrom to the myocardium Is configured to include a feedback sensor for mapping the penetration depth and location of the needle insertion. The use of a feedback sensor provides the advantage of accurately targeting the injection location. The target location for delivering the cell composition may vary. For example, an optimal treatment may require multiple small injections within a damaged/defective region where no two injections penetrate the same site. Alternatively, the target location may remain the same of successive cell administration procedures.

A suitable catheter that may be used in the present disclosure is the NOGA™ Injection Catheter system (Biosense Webster, Inc.). This catheter is a multi-electrode, percutaneous catheter with a deflectable tip and injection needle designed to inject agents into the myocardium. The tip of the Injection Catheter is equipped with a Biosense location sensor and a retractable, hollow 27-gauge needle for fluid delivery. The injection site is indicated in real-time on the heart map, allowing for precise distribution of the injections. Local electrical signals are obtained to minimize catheter-tip trauma.

Compositions of the Disclosure

In one example of the present disclosure the mesenchymal lineage precursor or stem cells and/or progeny thereof and/or soluble factor derived therefrom are administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other Ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to reduce, prevent or delay metabolic syndrome and/or obesity.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

The mesenchymal lineage precursor or stem cells and/or progeny thereof and/or soluble factor derived therefrom can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, (e.g., as described by Vacanti, at al. J. Ped. Surg. 23:3-9 1988; Cima, et al. Biotechnol. Bioeng. 38:145 1991; Vacanti, at al. Plast. Reconstr. Surg. 88:753-9 1991); or synthetic polymers such as polyanhydrides, polyorthoesters, and polylactic acid.

In another example, the mesenchymal lineage precursor or stem cells and/or progeny thereof and/or soluble factor derived therefrom may be administered in a gel scaffold (such as Gelfoam from Upjohn Company).

The compositions described herein may be administered alone or as admixtures with other cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of mesenchymal lineage precursor or stem cells and/or progeny thereof and/or soluble factor derived therefrom. For example, the composition comprises about $1 \times 10^6$ stem cells to about $1 \times 10^0$ stem cells or about $1.25 \times 10^3$ stem cells to about $1.25 \times 10^7$ stem cells/kg (80 kg subject). The exact amount of cells to be administered is dependent upon a variety of factors, including the age, weight, and sex of the subject, and the extent and severity of the disorder being treated.

Exemplary dosages include at least about $1.2 \times 10^8$ to about $8 \times 10^{10}$ cells, such as between about $1.3 \times 10^6$ to about $8 \times 10^9$ cells, for example, between about $1.4 \times 10^6$ to about $8 \times 10^8$ cells, for example, between about $1.5 \times 10^8$ to about $7.2 \times 10^8$ cells, between about $1.6 \times 10^8$ to about $6.4 \times 10^8$ cells, such as between about $1.7 \times 10^8$ to about $5.6 \times 10^8$ cells, for example, between about $1.8 \times 10^8$ to about $4.8 \times 10^8$ cells, for example, between about $1.9 \times 10^8$ to about $4 \times 10^8$ cells, between about $2.0 \times 10^8$ to about $3.2 \times 10^8$ cells, between about $2.1 \times 10^8$ to about $2.4 \times 10^8$ cells. For example, a dose can include at least about $2.0 \times 10^8$ cells. For example, a dose can include at least about $1.5 \times 10^8$ cells.

Expressed another way, exemplary doses include at least about $1.5 \times 10^8$ cells/kg. For example, a dose can comprise between about $1.5 \times 10^8$ to about $1 \times 10^9$ cells/kg, such as between about $1.6 \times 10^8$ to about $1 \times 10^8$ cells/kg, for example, between about $1.8 \times 10^8$ to about $1 \times 10^7$ cells/kg, for example, between about $1.9 \times 10^8$ to about $9 \times 100$ cells/kg, between about $2.0 \times 10^8$ to about $8 \times 10^8$ cells/kg, such as between about $2.1 \times 10^8$ to about $7 \times 10^8$ cells/kg, for example, between about $2.3 \times 10$ to about $6 \times 10^8$ cells/kg, for example, between about $2.4 \times 10^6$ to about $5 \times 10W$ cells/kg, for example, between about $2.5 \times 10^8$ to about $4 \times 10^6$ cells/kg, for example, between about $2.6 \times 10^8$ to about $3 \times 10^6$ cells/kg. For example, a dose can include at least about $2.5 \times 10^8$ cells/kg.

In an example, the mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% of the cell population of the composition.

Compositions of the disclosure may be cryopreserved. Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cryopreservation solution may comprise a sterile, non-pyrogenic Isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, USP ($C_2H_3NaO_2 \cdot 3H_2O$); 37 mg of potassium chloride, USP (KCl); and 30 mg of magnesium chloride, USP ($MgCl_2 \cdot 6H_2O$). It contains no antimicrobial agents. The pH Is adjusted with sodium hydroxide. The pH is 7.4 (6.5 to 8.0).

The cryopreservation solution may comprise Profreeze™. The cryopreservation solution may additionally or alternatively comprise culture medium, for example, αMEM.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methycellulose, polyvinyl pyrrolidone (PVP) and trehalose.

In one embodiment, cells are suspended in 42.5% Profreeze™/50% αMEM/7.5% DMSO and cooled in a controlled-rate freezer.

The cryopreserved composition may be thawed and administered directly to the subject or added to another solution, for example, comprising HA. Alternatively, the cryopreserved composition may be thawed and the mesenchymal lineage precursor or stem cells resuspended in an alternate carrier prior to administration.

In an example, the compositions described herein may be administered between about 1 and about 10 days post MI.

In other examples, the compositions described herein may be administered between about 1 and 9 days, between about 1 and 8 days, between about 2 and 7 days, between about 2 and 6 days, between about 3 and 5 days post MI. For example, the compositions described herein may administered about 5 days post-MI.

In an example, the compositions described herein may be administered between about 1 and about 10 days post percutaneous coronary intervention (PCI).

In other examples, the compositions described herein may be administered between about 1 and 9 days, between about 1 and 8 days, between about 2 and 7 days, between about 2 and 6 days, between about 3 and 5 days post PCI. For example, the compositions described herein may administered about 5 days post PCI.

In an example, the compositions described herein may be administered as a single dose.

In some examples, the compositions described herein may be administered over multiple doses. For example, at least 2, at least 3, at least 4, at least 5, at least 6, at least 7, at least 8, at least 9, at least 10 doses.

In one example, the mesenchymal lineage precursor or stem cells can be culture expanded prior to administration. Various methods of cell culture are known in the art.

In an example, mesenchymal lineage precursor or stem cells are culture expanded in a serum free medium prior to administration.

In some examples, the cells are contained within a chamber that does not permit the cells to exit into a subject's circulation but permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., Implanted in or near the heart.

The mesenchymal lineage precursor or stem cells and/or progeny thereof and/or soluble factor derived therefrom cells may be administered systemically, such as, for example, by intravenous, intraarterial, or intraperitoneal administration. The mesenchymal lineage precursor or stem cells and/or progeny thereof and/or soluble factor derived therefrom may also be administered by intramuscular or intracardiac administration.

In an example, the mesenchymal lineage precursor or stem cells and/or progeny thereof and/or soluble factor derived therefrom are administered directly into the myocardium. For example, the mesenchymal lineage precursor or stem cells and/or progeny thereof and/or soluble factor derived therefrom can be administered directly into the myocardium of the left ventricle.

In an example, the mesenchymal lineage precursor or stem cells and/or progeny thereof and/or soluble factor derived therefrom are administered via an endomyocardial catheter such as the J&J Myostar™ injection catheter.

In an example, the mesenchymal lineage precursor or stem cells and/or progeny thereof and/or soluble factor derived therefrom are administered to viable myocardium.

In an example, the mesenchymal lineage precursor or stem cells and/or progeny thereof and/or soluble factor derived therefrom are administered to hibernating myocardium.

One of skill in the art would be able to Identify viable and/or hibernating myocardium using methods known in the art. For example, a mapping catheter system such as the NOGASTAR™ Mapping Catheter system can be used to identify viable and/or hibernating myocardium.

In another example, the mesenchymal lineage precursor or stem cells and/or progeny thereof and/or soluble factor derived therefrom are administered via intracoronary Infusion. For example, mesenchymal lineage precursor or stem cells and/or progeny thereof and/or soluble factor derived therefrom may be administered into the left anterior descending (LAD) artery.

In an example, mesenchymal lineage precursor or stem cells and/or progeny thereof and/or soluble factor derived therefrom are administered into the LAD artery immediately after LAD revascularisation via PCI.

Six minute walk test (6MWT)

The six minute walk test (6MWT) was developed in 1963 (Balke B et al (1963) Rep Civ Aeromed Res Inst US 53:1-8) to evaluate exercise tolerance in chronic respiratory disease and heart failure. The test measures the distance an subject is able to walk over a total of six minutes on a hard, flat surface. The goal is for the subject to walk as far as possible in six minutes. The subject is allowed to self-pace and rest as needed as they traverse back and forth along a marked walkway.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The following specific examples are to be construed as merely illustrative, and not limitative of the remainder of the disclosure in any way whatsoever. Without further elaboration, it is believed that one skilled in the art can, based on the description herein, utilize the present Invention to its fullest extent.

EXAMPLES

Example 1 Study Design

A study was conducted to evaluate the safety and tolerability of 3 Increasing doses (25, 75 or 150 million cells) of mesenchymal precursor cells (MPCs) in subjects with heart failure due to left ventricular systolic dysfunction of either ischemic or non-ischemic etiology. The secondary objectives were to look at efficacy via multiple parameters, and to Identify an optimal effective dose and optimal target population for MPC treatment.

The heart failure subjects were >18 years of age; heart failure caused by ischemic or non-ischemic cardiomyopathy, LV systolic dysfunction shown by an ejection fraction (EF) of <30% detected on radionuclide ventriculography, two-dimensional echocardiography or nuclear magnetic resonance imaging; and echocardiographically determined LV end-diastolic diameter>3.2 cm/m$^2$ or >6 cm; symptoms of dyspnoea or fatigue at rest or at minimal exertion (New York Heart Association (NYHA) class II or ill) for >2 months; at least one hospitalisation or two outpatient visits requiring intravenous diuretic or vasodilator therapy within 12 months before screening; and optimal medical therapy including diuretics, beta blockers, and angiotension-converting enzyme (ACE)-inhibitors or angiotension receptor blockers (ARBs) unless intolerant or contraindicated.

Subjects were excluded based on acute myocardial Infarction in the previous 90 days, serum potassium<4.0 or >5.5 mEq/L, digoxin levels>1.2 ng/mL, magnesium levels<1.0 mEq/L, serum creatinine>2.0 mg/dL and serum bilirubin>3.0 mg/dL.

Subjects were randomized to either an injection of 25, 75 or 150 million MPC by endomyocardial catheter or scripted mock injections (control group) in the catheterization laboratory. MPCs were administered Into the left ventricle (approximately 15-20 injections of 0.2 ml/injection) using the J&J Myostar™ injection catheter and NOGASTAR™ Mapping Catheter system that identifies viable/hibernating myocardium based on electrical voltage, theoretically making targeting of healthy but at risk tissue easier. This catheter has the largest safety profile for this application and has been used in over 1,000 patients across multiple trials. Measurement of functional efficacy involved left ventricular end systolic volume, or LVESV, and left ventricular end diastolic volume, or LVEDV, measurements as well as left ventricular ejection fraction, or LVEF. An additional time-to-first event analysis of heart failure-related major adverse cardiac events, or HF-MACE, was performed. HF-MACE was defined as a composite of cardiac related death or resuscitated cardiac death, or non-fatal decompensated heart failure events.

Endomyocardial injections of MPCs in patients with chronic heart failure were feasible and safe. The Incidence of adverse events was similar across all groups, and there was no clinically significant immune response in any patients who received MPCs.

The 150 million cell dose showed the greatest effect on left ventricular remodeling and functional capacity and a threshold benefit for reducing HF-MACE long-term (FIG. 1).

More specifically, there was a dose-related effect on both LVESV and LVEDV, with the 150 million cell dose showing the greatest effect compared to controls for LV remodeling (LVESV and LVEDV both p<0.02) at month 6 post treatment and functional exercise capacity as measured by six minute walk test (6MTW: p=0.062) at month 12 post treatment. A p-value Is a probability, ranging in value from 0 to 1, which indicates the likelihood that the results of a study are different between treatment and control groups. The lower the p-value, the harder it would be to see the results by chance alone. P-values below 0.05 are typically referred to as statistically significant.

Figure 2:
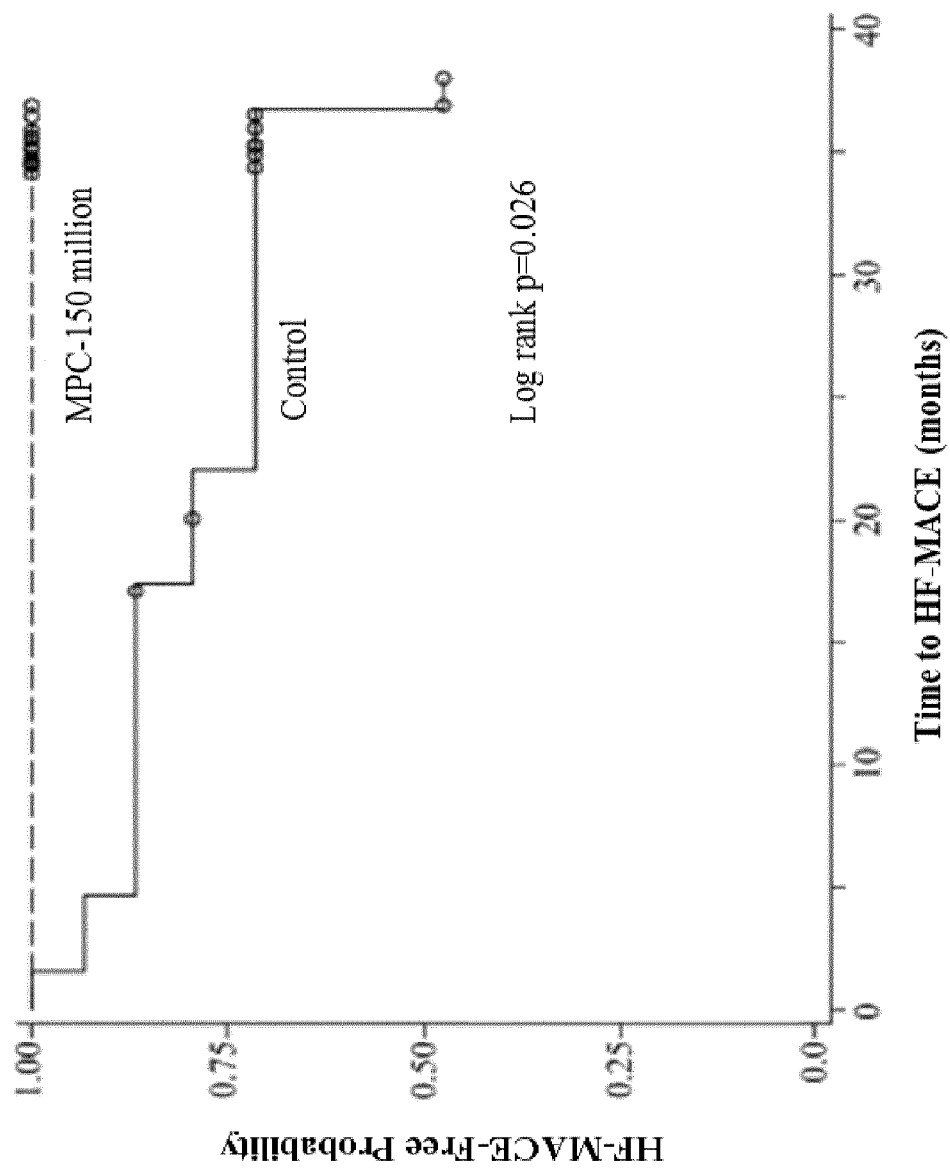
FIG. 2 shows HF-MAC by Kaplan-Meier Curve 36 months post treatment with 150 million MPCs.

An independent blind adjudication of potential HF-MACE was conducted post-hoc. Over 36 months of follow up, the 150 million cell dose was associated with a significantly greater probability of remaining free of HF-MACE events compared to the control group (0% versus 33% HF-MACE by Kaplan-Meier, p=0.026 by log-rank). The 25 and 75 million doses were not statistically different than controls with respect to this measure. On the basis of these results, the optimal dose for therapeutic benefit was considered to be the 150 million MPC dose (FIG. 2).

Example 2 Therapeutic Benefit of MPC Administration on Parameters of Cardiac Function (Intention to Treat Analysis)

In order to Identify the most appropriate target population for the 150 million MPC dose, the inventors evaluated whether optimal responders to MPC therapy were in the groups with more or less advanced heart failure. A further post-hoc analysis was performed in a blinded manner stratifying controls or 150 million MPC treated patients into those with a baseline LVESV of either less than or greater than 100 ml as a surrogate for significant myocardial contractile abnormality and advanced heart failure. The 100 ml LVESV threshold was chosen because it falls more than 3 standard deviations above normal LVESV.

Table 1 below shows the analysis of a comparison of all subjects (i.e. those having a LVEF of any value) versus subjects with a LVESV>100 in an intent to treat population.

Intention to treat analysis is a statistical concept. According to Fisher et al. (Fisher L D, Dixon D O, Herson J, Frankowski R K, Hearron M S, Peace K E. Intention to treat in clinical trials. In: Peace K E, editor. Statistical issues in drug research and development. New York: Marcel Dekker: 1990. pp. 331-50. (1990)), the ITT analysis includes all randomized patients in the groups to which they were randomly assigned, regardless of their adherence with the entry criteria, regardless of the treatment they actually received, and regardless of subsequent withdrawal from treatment or deviation from the protocol. In other words, ITT analysis includes every subject who is randomized according to randomized treatment assignment. It ignores noncompliance, protocol deviations, withdrawal, and anything that happens after randomization. ITT analysis avoids overoptimistic estimates of the efficacy of an Intervention resulting from the removal of non-compliers by accepting that noncompliance and protocol deviations are likely to occur in actual clinical practice.

TABLE 1

Comparison of all subjects versus subjects with LVESV >100 ml (ITT, or intention to treat)

| | Change (Entire Cohort) Baseline to month 6 | | | Change (LVESV >100 ml Cohort) Baseline to month 6 | | | |
|---|---|---|---|---|---|---|---|
| | Control (n = 15) | MPC-IM-150 (n = 15) | Change relative to control | Control (n = 7) | MPC-IM-150 (n = 11) | Change relative to control | P-values |
| LVESV (ml) | +20 | −7 | −27 | +46 | −8 | −54 | <0.02 |
| LVEDV (ml) | +20 | −10 | −30 | +41 | −10 | −51 | <0.03 |
| LVEF (%) | −2.3 | +0.6 | +2.9 | −6.4 | +1.7 | +8.1 | <0.05 |

This analysis demonstrated that the therapeutic benefit of the 150 million dose on parameters of LV remodeling were markedly amplified by focusing on the target population with substantial baseline LV contractile abnormality and advanced heart failure (LVESV greater than 100 ml).

Example 3 Therapeutic Benefit of MPC Administration on LVESV

A total of 30 subjects (being a mixture of heart failure and non-heart failure subjects) were evaluated for baseline LVESV level. The distribution of the subjects is shown in Table 2. Subjects were categorised Into placebo group or MPC cell group (which were administered $1.5 \times 10^8$ mesenchymal precursor cells (MPCs)). Injection was into the left ventricle (approximately 15-20 injections of 0.2 ml/injection) using the J&J Myostar Injection catheter and NOGASTAR Mapping catheter system that Identifies viable/hibernating myocardium based on electrical voltage. Subjects were stratified on the basis of their left ventricular end systolic volume (LVESV) value of either <100 mL or >100 mL.

TABLE 2

Stratification of subjects according to baseline LVESV value

| | Baseline LVESV ≤100 mL | | Baseline LVESV >100 mL | |
|---|---|---|---|---|
| | Placebo/control | MPC cell group | Placebo/control | MPC cell group |
| Total no. of subjects | 8 | 4 | 7 | 11 |
| NYHA class II | 3 | 3 | 3 | 9 |
| NYHA class III | 5 | 1 | 4 | 2 |

Of the 30 subjects evaluated for the study, 18 subjects had a baseline LVESV value of >100 mL. Seven (7) subjects were assigned to placebo and 11 assigned to MPC.

Figures 1, 3:
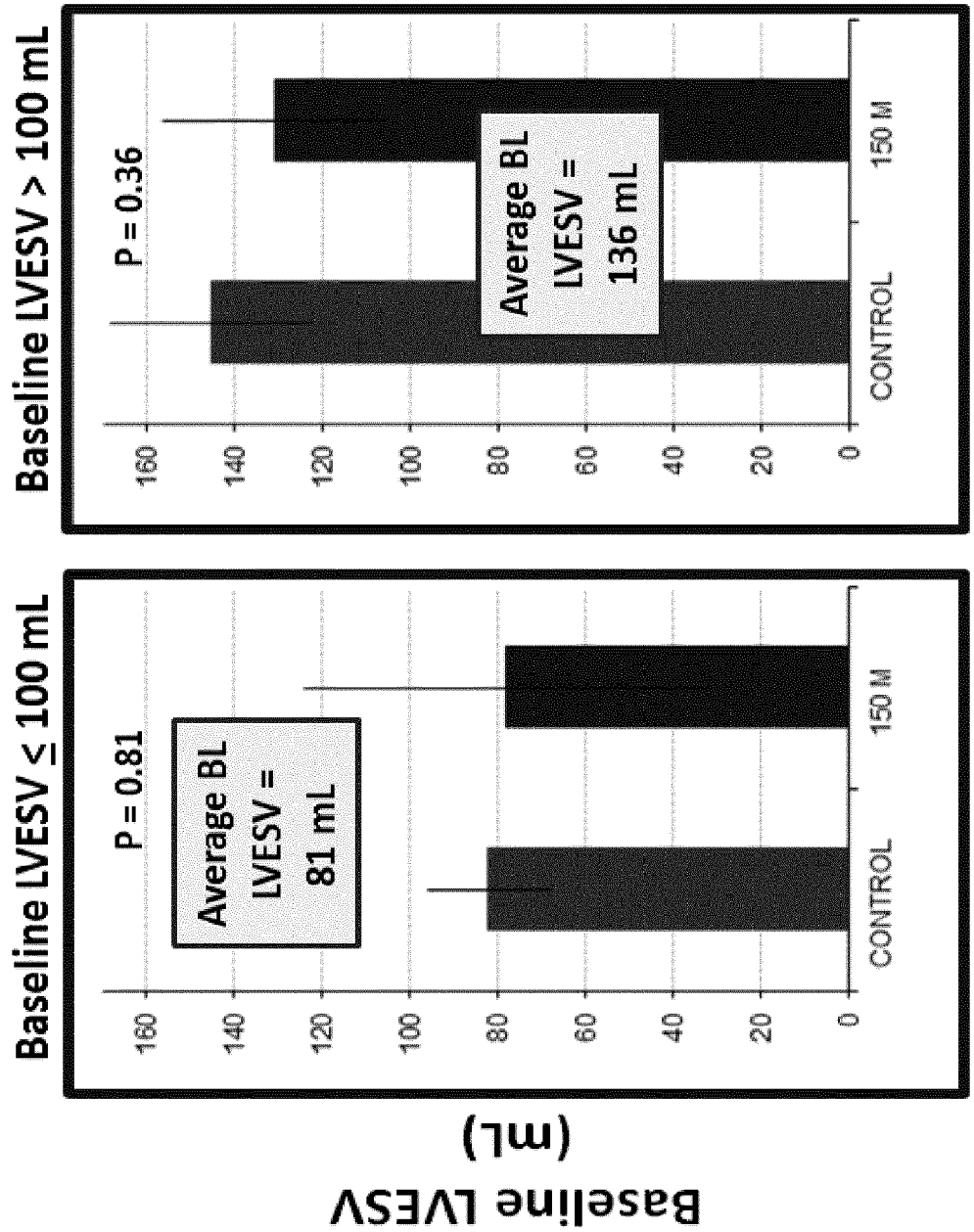
Figures 2, 3:
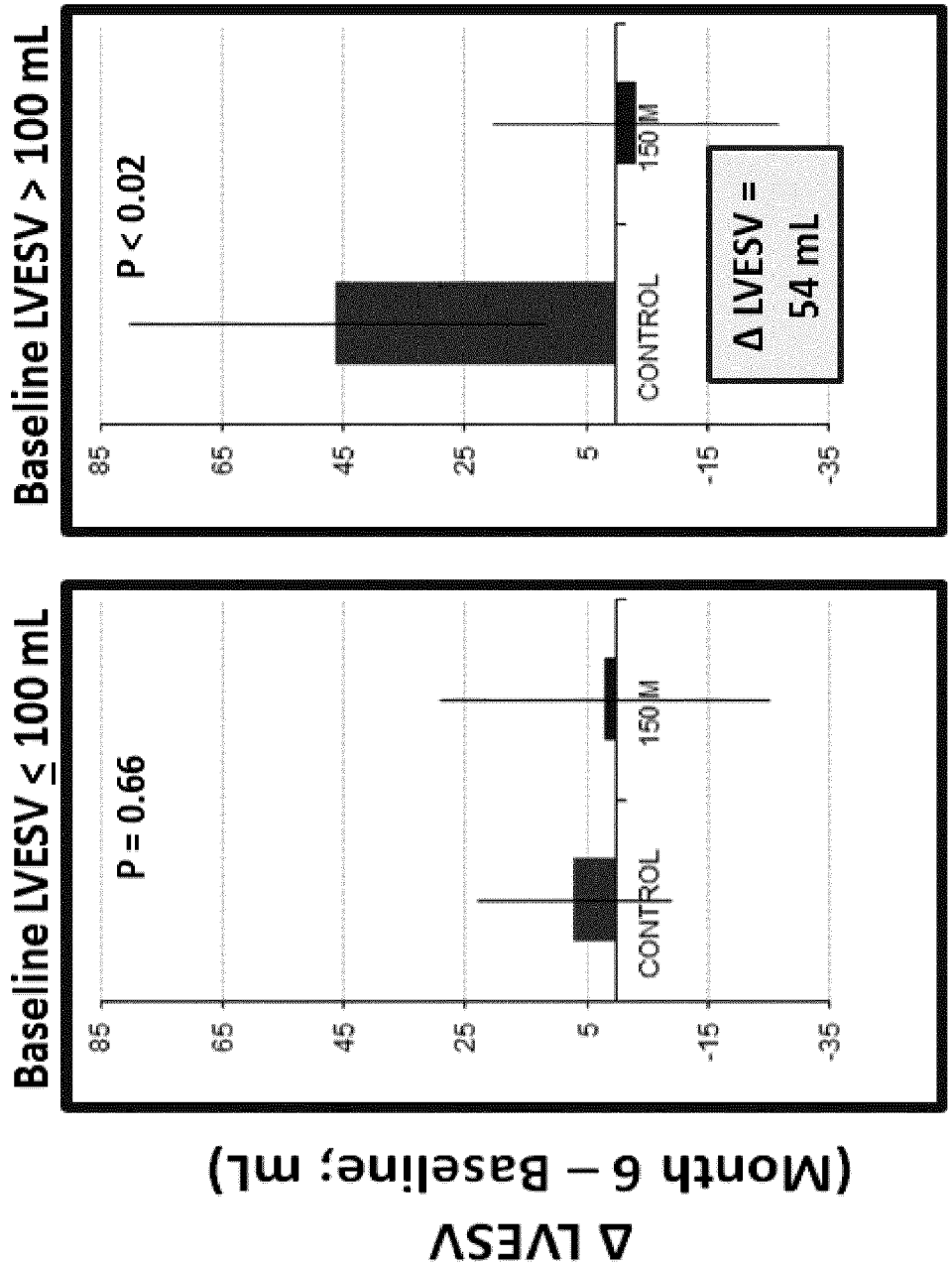

FIG. 3-1 shows the baseline LVESV values for the subject groups. Subjects stratified according to their LVESV of less than or equal to (≤1100 mL had an average baseline LVESV value of 81 mL. Subjects stratified according to their LVESV value of greater than (>) 100 mL had an average baseline value of 136 mL.

Subjects were re-evaluated at the 6 month time point following administration of placebo or $1.5 \times 10^8$ mesenchymal precursor cells (MPCs). The major adverse cardiac event (MACE) rate was determined for the subjects stratified on the basis of LVESV value. The results are shown in FIG. 3-2 represented as a change in LVESV value between the baseline and 6 month time points. The change in LVESV value between placebo (control) and subjects administered MPCs was statistically significant.

Table 3 shows the heart failure MACE rate (HF-MACE) in numerical and percentage values.

TABLE 3

Change in LVESV values in subjects stratified according to baseline LVESV value

| | Baseline LVESV ≤100 mL | | Baseline LVESV >100 mL | |
|---|---|---|---|---|
| | Placebo/control | MPC cell group | Placebo/control | MPC cell group |
| Total no. of subjects | 8 | 4 | 7 | 11 |
| HF-MACE (n) | 0 | 0 | 5 | 0 |
| HF-MACE (%) | 0 | 0 | 71% | 0 |
| HF-MACE (BL NYHA) | NA | NA | Class II = 2 Class III = 3 | |

Subjects with baseline LVESV values<100 mL did not develop a major adverse cardiac event at the 6 month evaluation period, this was irrespective of whether the subject was administered placebo or $1.5 \times 10^6$ mesenchymal precursor cells (MPCs). HF-MACE occurred only in placebo subjects (control) with evidence of greater baseline cardiac dysfunction as assessed by LVESV>100 mL. In contrast, none of the subjects with baseline cardiac dysfunction as assessed by LVESV>100 mL administered MPCs developed HF-MACE.

The data in Table 2 demonstrate that subjects with heart failure treated with placebo will experience a high MACE rate (i.e. 71% at the 6 month period). In particular, the high MACE rate is only observed in subjects having a baseline LVESV value of >100 mL.

The data shows that heart failure subjects with a baseline LVESV value of >100 mL achieve optimal treatment benefit from the administration of MPCs. In other words, subjects with the highest risk of disease progression achieved the greatest benefit from the administration of MPCs.

Example 4 Therapeutic Benefit of MPC Administration on LVEDV and LVEF

The left ventricular end diastolic volume (LVEDV) was also evaluated in subjects that had been stratified according to LVESV value less than or equal to (≤) 100 mL. or >100 ml.

Figures 1, 4:
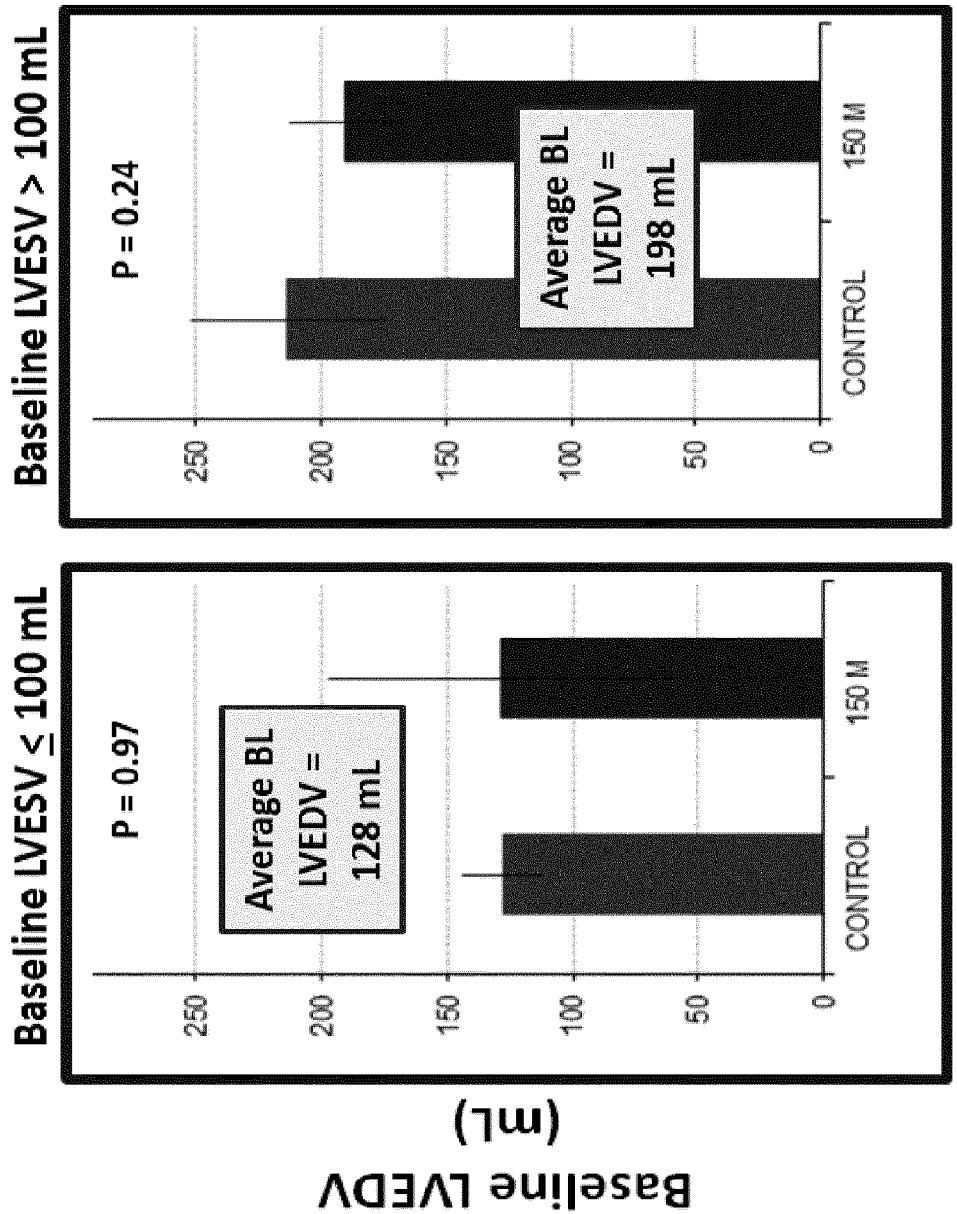
Figures 2, 4:
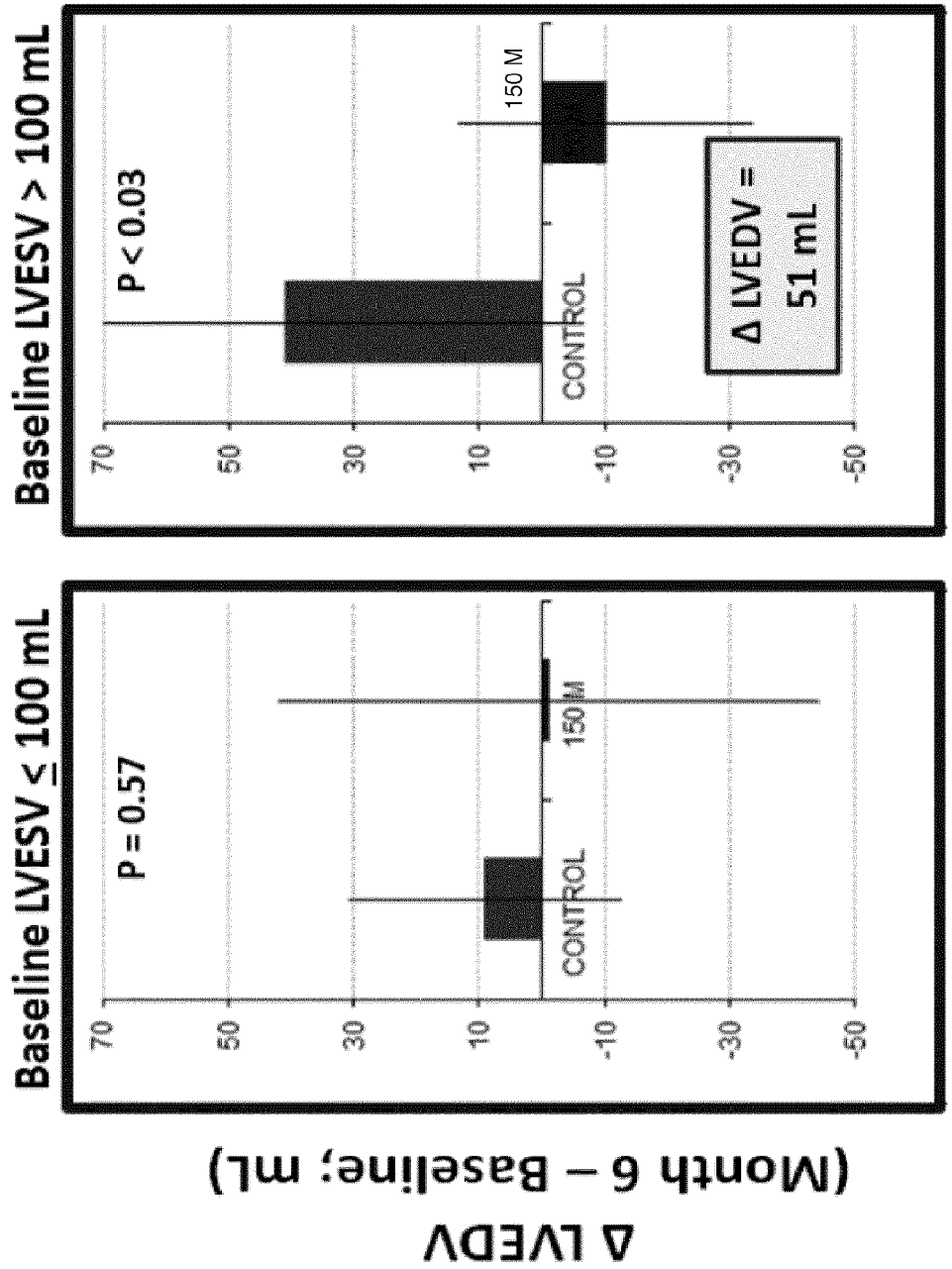

FIG. 4-1 shows the baseline LVEDV values for the subjects. Subjects with a baseline LVESV of ≤100 mL had an average baseline LVEDV of 128 mL. Subjects with a baseline LVESV value of >100 mL had an average baseline LVEDV value of 198 mL.

Subject distribution is as per Table 1.

FIG. 4-2 shows the change in LVEDV value at 6 months following administration of placebo (control) or MPCs between subjects striated according to baseline LVESV of ≤100 mL and baseline LVESV of >100 mL. The figure shows that heart failure subjects with the highest MACE rate achieve therapeutic benefit from the administration of MPCs as demonstrated by improvement in LVEDV value. The difference between subjects striated according to LVESV value≤100 mL or >100 mL was statistically significant.

Figures 1, 5:
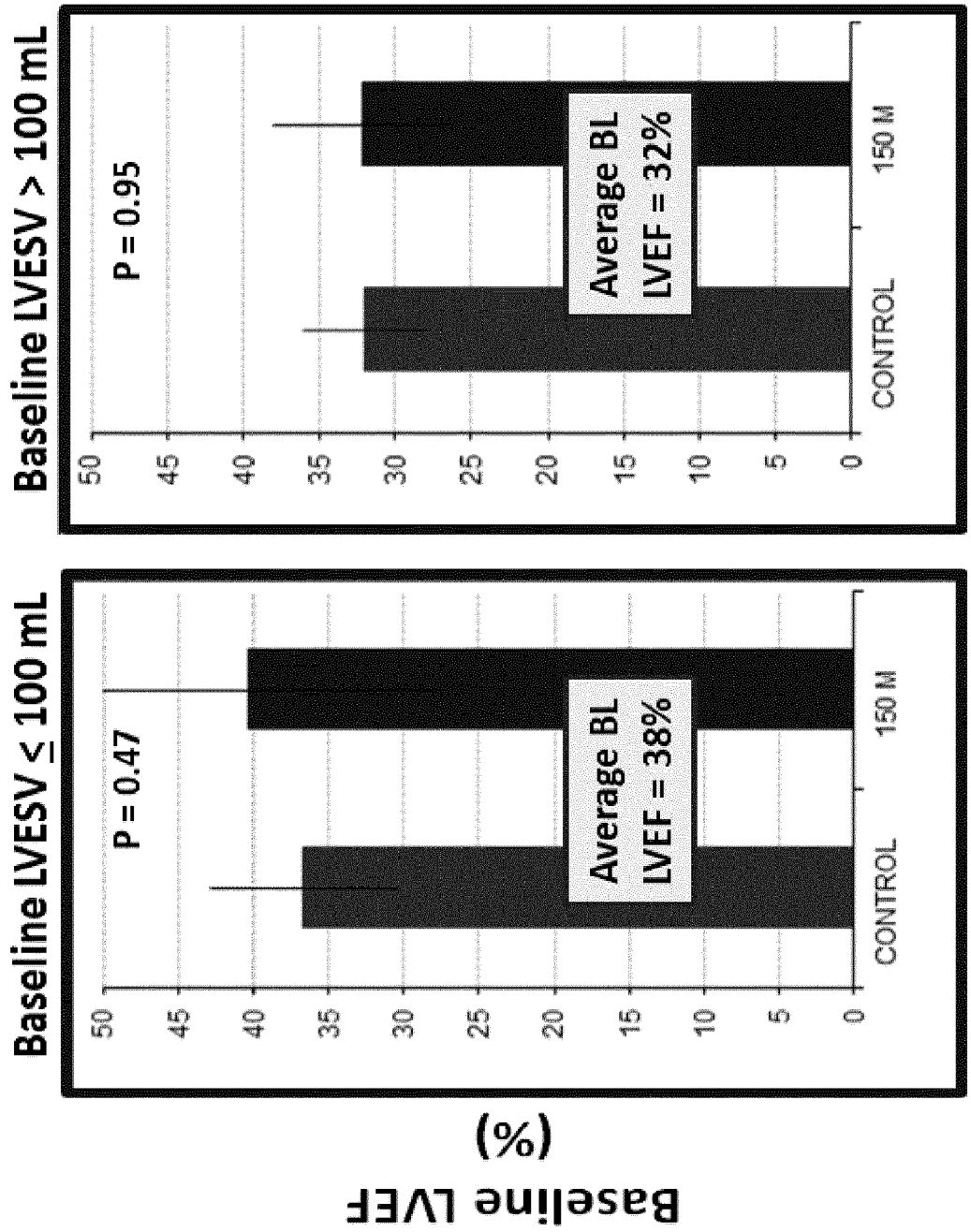
Figures 2, 5:
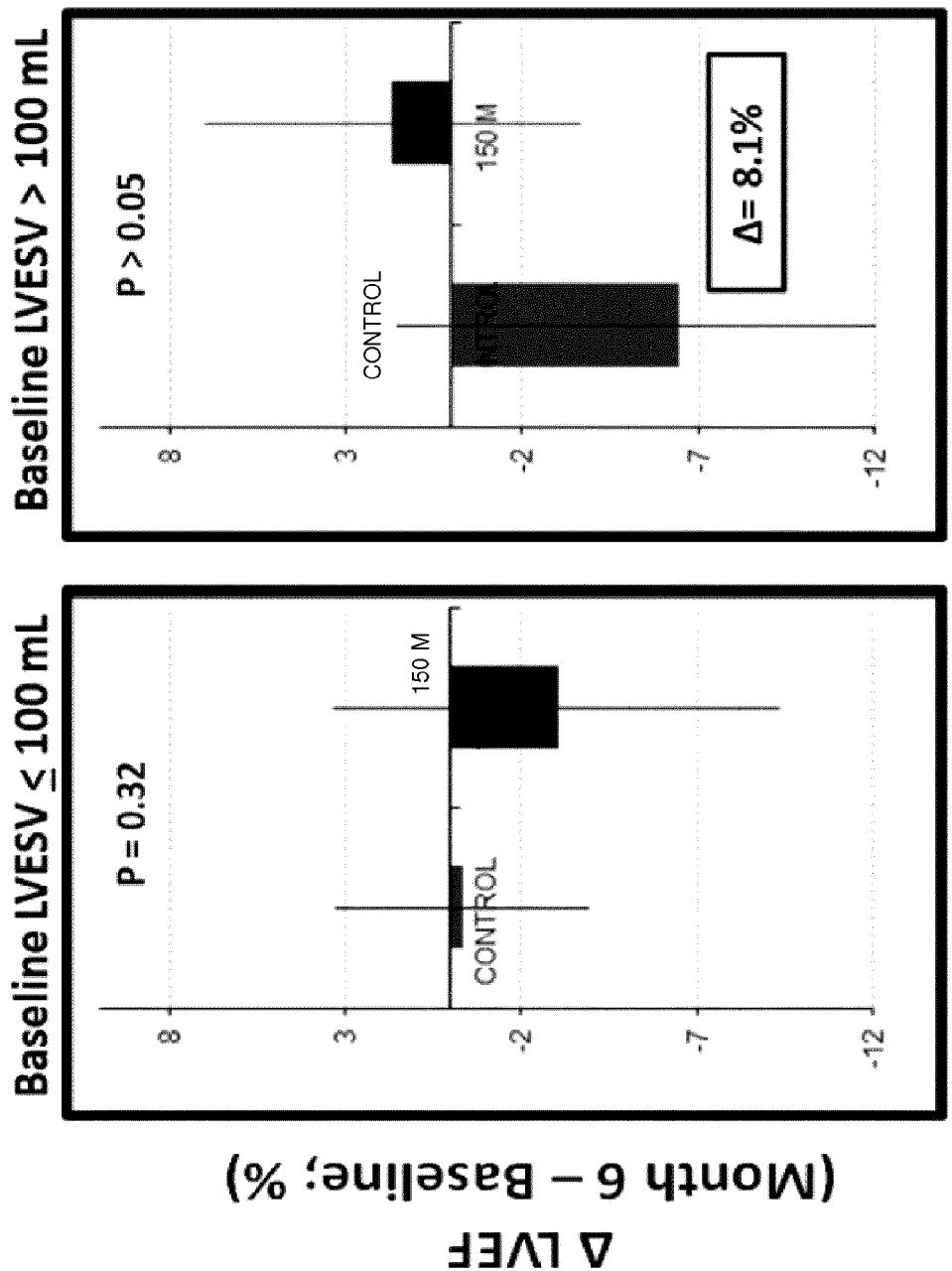
Figure 6:
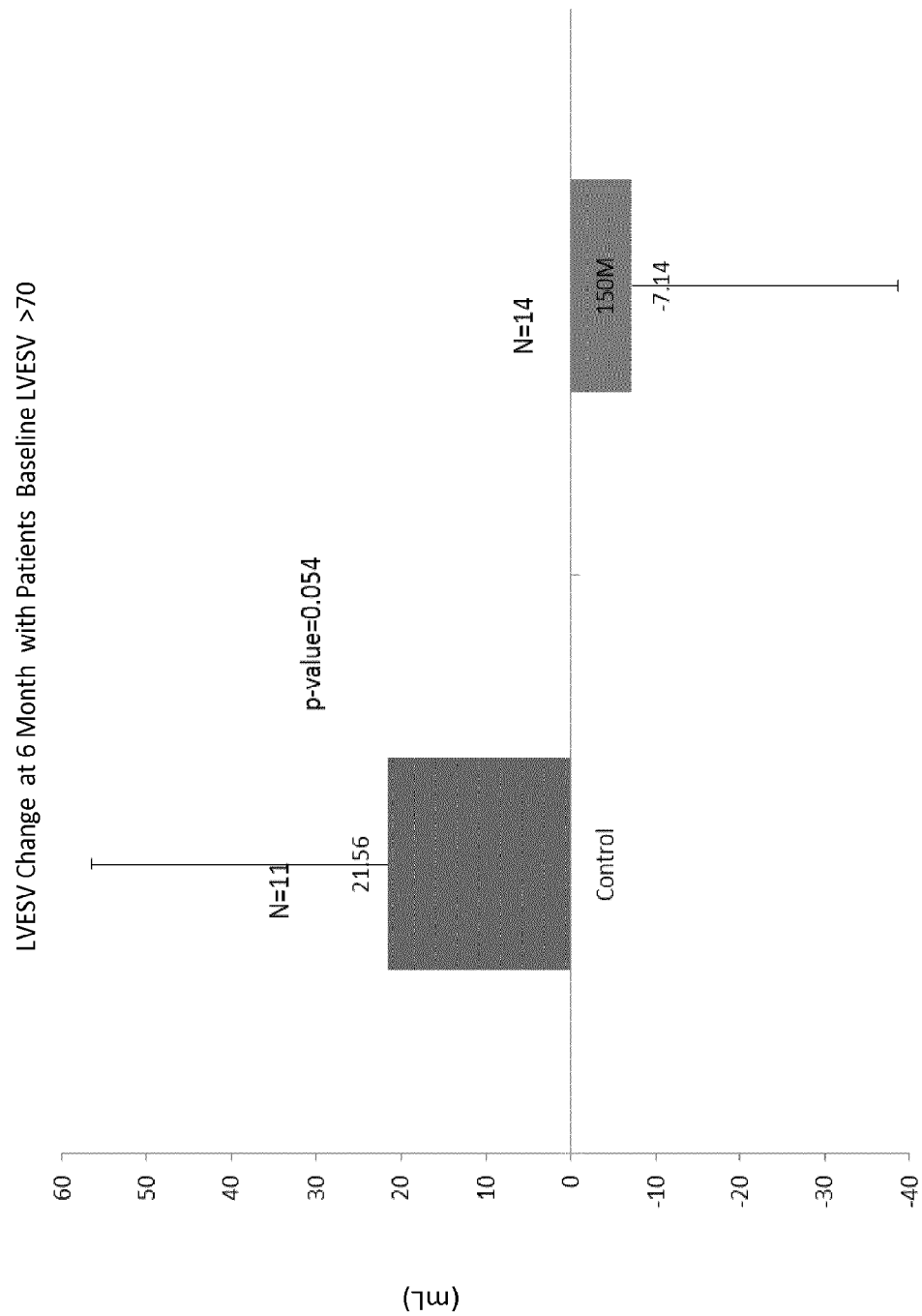
Figure 7:
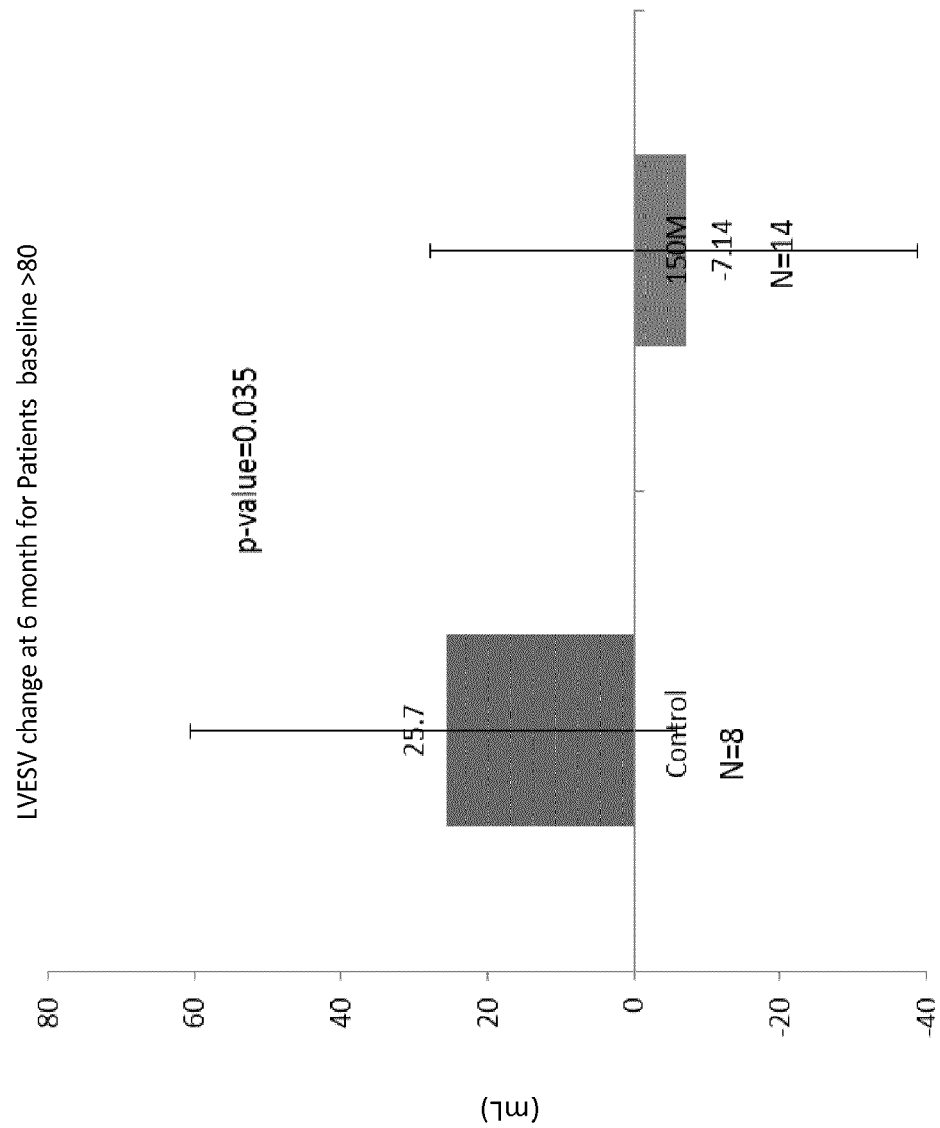
FIG. 7 shows the change in LVESV value at 6 months in placebo (control) and MPC administered subjects (150 million cells) striated according to a LVESV of greater than 80 mL.
Figure 8:
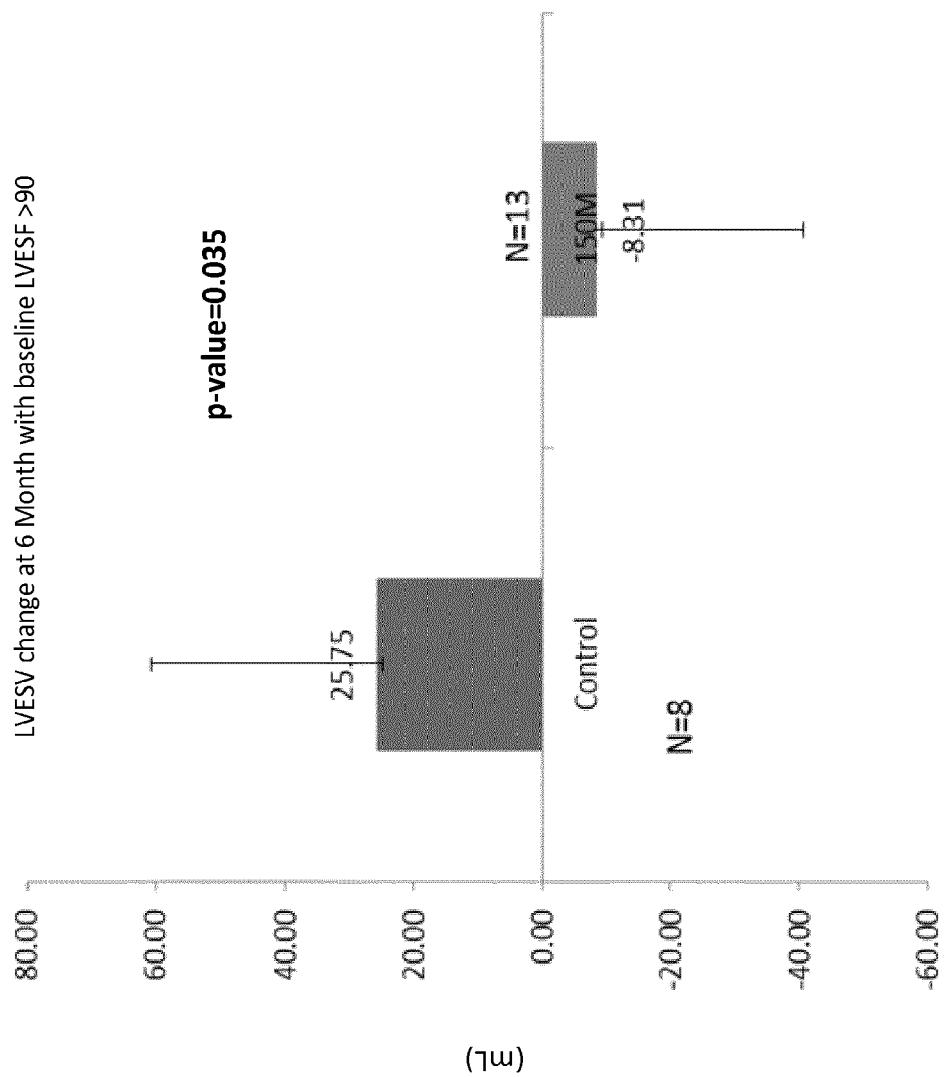
FIG. 8 shows the change in LVESV value at 6 months in placebo (control) and MPC administered subjects (150 million cells) striated according to a LVESV of greater than 90 mL.
Figure 9:
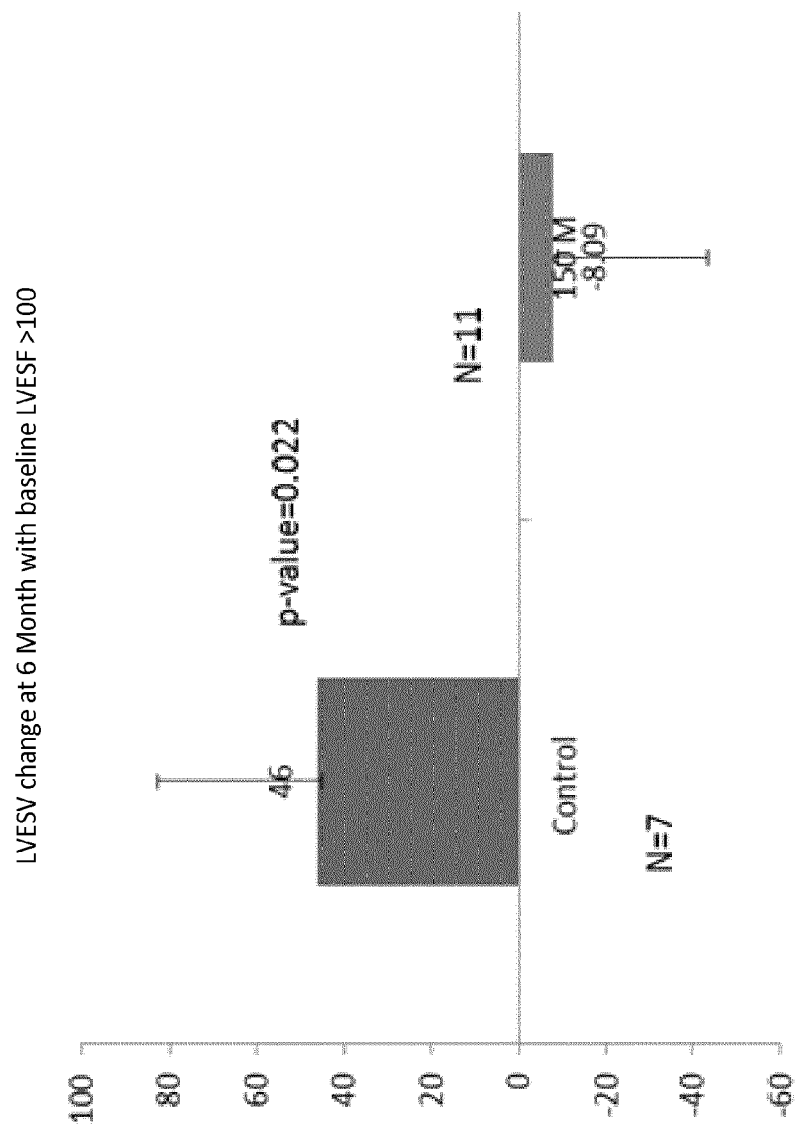
FIG. 9 shows the change in LVESV value at 6 months in placebo (control) and MPC administered subjects (150 million cells) striated according to a LVESV of greater than 100 mL.
Figure 10:
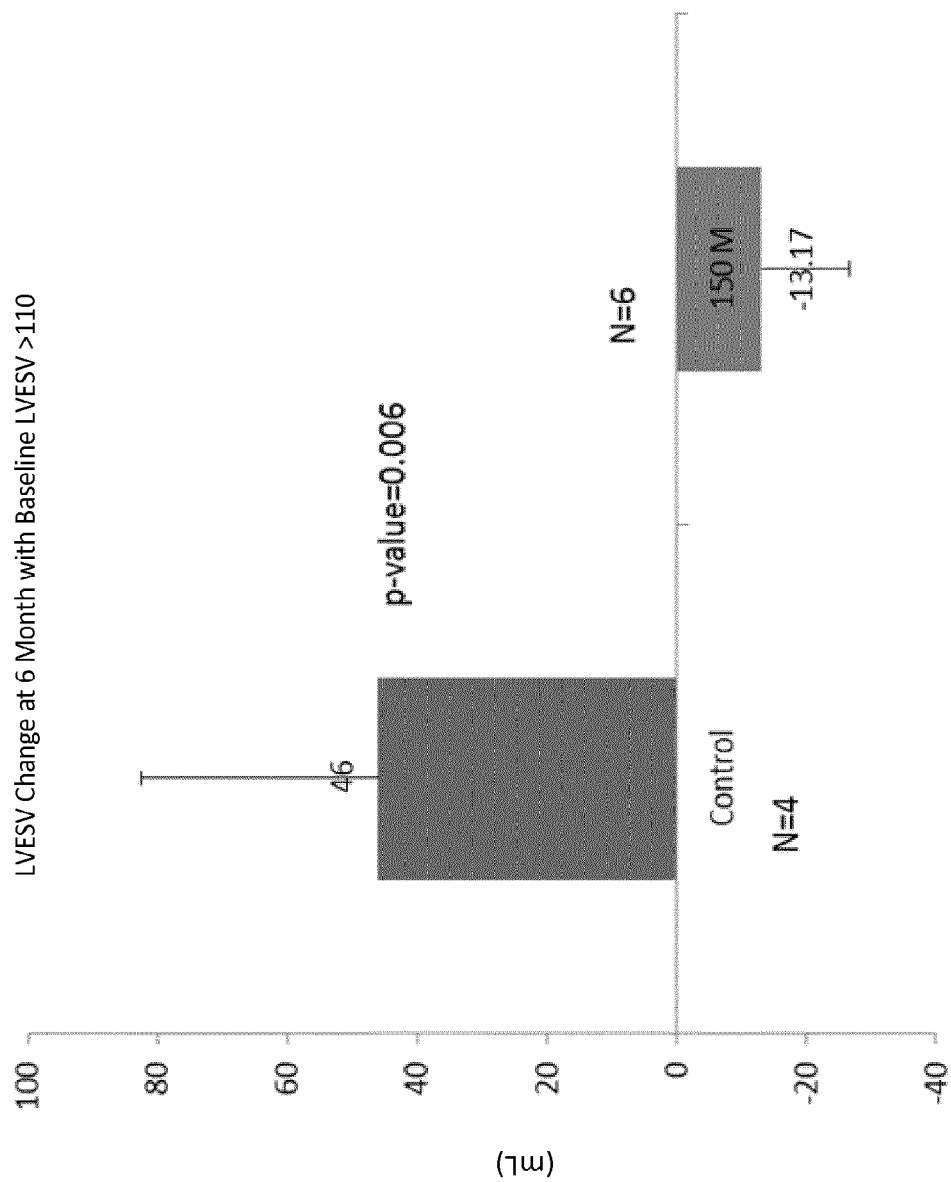
FIG. 10 shows the change in LVESV value at 6 months in placebo (control) and MPC administered subjects (150 million cells) striated according to a LVESV of greater than 110 mL.
Figure 11:
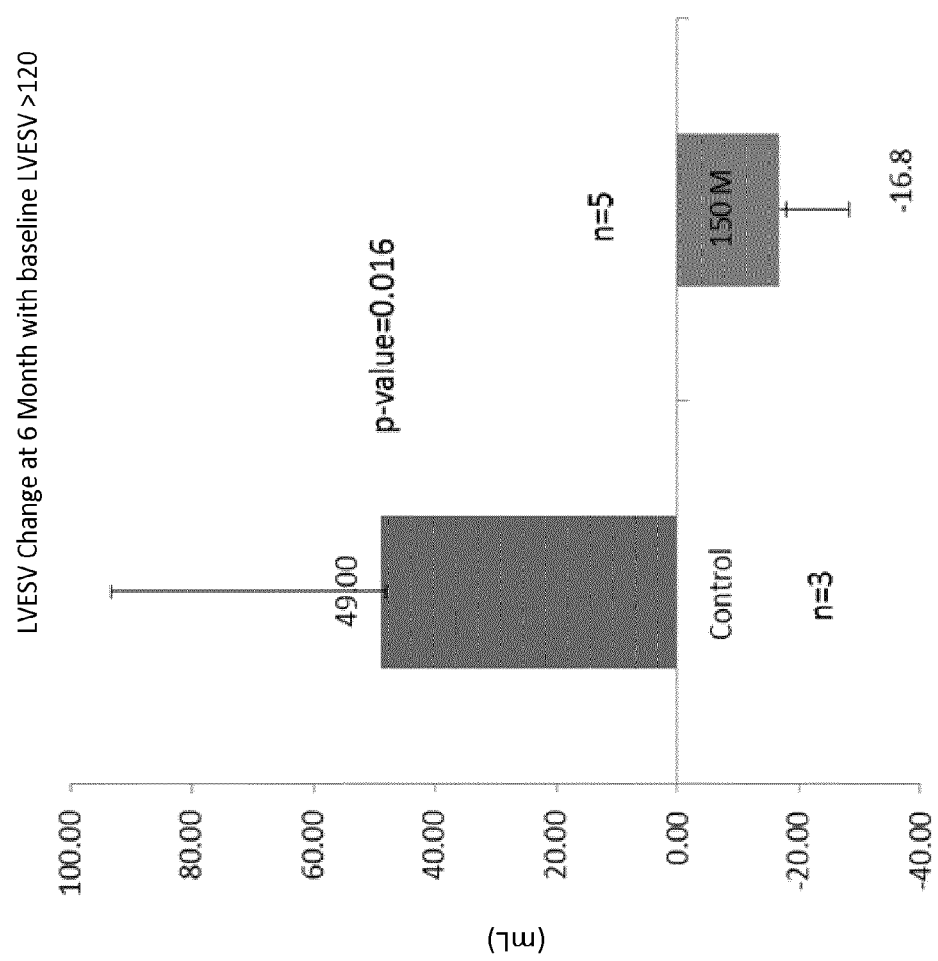
FIG. 11 shows the change in LVESV value at 6 months in placebo (control) and MPC administered subjects (150 million cells) striated according to a LVESV of greater than 120 mL.

The left ventricular ejection fraction (LVEF) value was also evaluated in subjects that had been stratified according to their LVESV value. FIG. 5-1 shows the baseline LVEF values for the subjects. Subjects with a baseline LVESV of ≤100 mL had an average baseline LVEF of between 35-40%. Subjects with a baseline LVESV value of >100 mL had an average baseline LVEF value of about 32%.

Subject distribution is as for Table 1.

FIG. 5-2 shows the change in LVEF value at 6 months following administration of placebo (control) or MPCs between subjects striated according to baseline LVESV of <100 mL and baseline LVESV of >100 mL. The figure shows that heart failure subjects with the highest MACE rate achieve therapeutic benefit from the administration of MPCs as demonstrated by Improvement in LVEF value. The difference between subjects striated according to LVESV value<100 mL or >100 mL was statistically significant.

Example 5 Correlation Between Disease Severity and Therapeutic Benefit of MPC on LVESV A further sensitivity analysis across every decile in baseline LVESV between 70 ml and 120 ml confirmed the findings seen in the stratification using a LVESV greater than 100 ml.

FIGS. 6 through 11 show the change in LVESV in subjects evaluated at 6 months following administration of placebo (control) or MPCs ($1.5 \times 10^8$ mesenchymal precursor cells). The reduction in LVESV was correlated with the level of heart failure (as determined by measurement of baseline LVESV). Subjects were striated according to LVESV as shown in Table 4 below.

TABLE 4

Change in LVESV

| LVESV cut-off value | Change in LVESV at 6 months | | |
|---|---|---|---|
| | Placebo/control | MPC cell group | P value |
| >70 mL | 21.56 | −7.14 | 0.054 |
| >80 mL | 25.7 | −7.14 | 0.035 |
| >90 mL | 25.75 | −8.31 | 0.035 |
| >100 mL | 46 | −8.09 | 0.022 |
| >110 mL | 46 | −13.17 | 0.006 |
| >120 mL | 49 | −16.8 | 0.016 |

Example 6 HF-MACE in Patients with LVESV>100 ml

Figure 12:
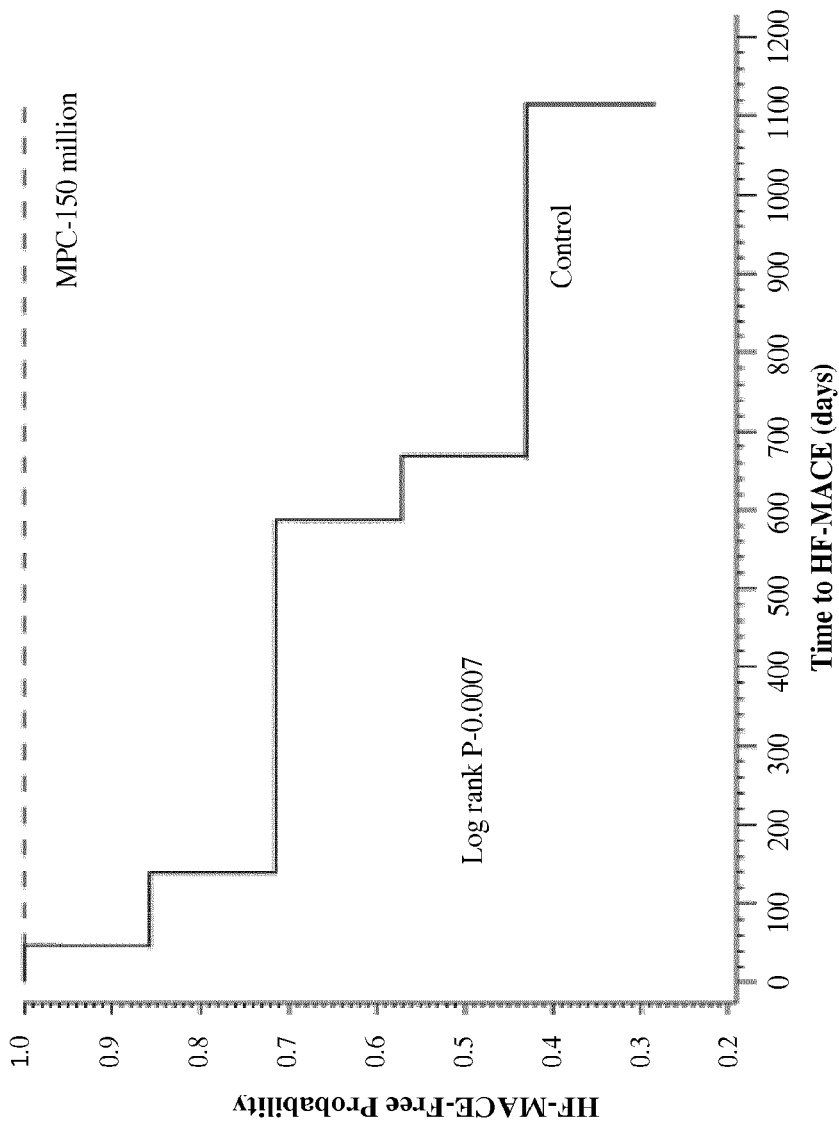
FIG. 12 shows MF-MACE Kaplan-Meier curve at 36 months post-treatment in patients with LVESV>100 ml.

HF-MACE was examined at 36 months post-treatment in controls and subjects receiving 150 million MPCs. All of the HF-MACE events over 36 months of follow-up occurred exclusively in the controls with advanced heart failure (FIG. 12).

The annualized HF-MACE rate in these fast progressors was 24%, compared with 11% in all of the controls.

More specifically, among 18 Class II/III CHF patients with baseline LVESV>100 ml, 5/7 (71%) placebo-treated versus 0/11 150 million MPC-treated experienced one or more HF-MACE events over 36 months (p=0.0007).

Therefore, the effect of the 150 million MPC dose on overall HF-MACE was markedly amplified in those patients with advanced heart failure and a high rate of progression and this may represent the optimal target patient population for MPC therapy.

Remarks

The data shown herein demonstrate that the greater the magnitude of baseline left ventricular contractile abnormality in subjects with chronic heart failure due to left ventricular systolic dysfunction, the more beneficial the MPC-related cardioprotective effect observed over a 8 month follow-up period. The data further demonstrates that the progressive adverse natural history associated with advance chronic heart failure can be beneficially altered by treatment with MPCs. Without wishing to be bound by theory, the findings are supportive of the paracrine cross-talk hypothesis in which tissue level biochemical/physiologic derangements create a local environment that facilitates MPC release of beneficial paracrine mediators. Thus the optimal benefit achieved by administration of MPCs in heart failure subjects, is seen in those subjects with the highest risk of disease progression, namely subjects with a baseline LVESV of >70 mL.

Baseline LVESV>70 ml identified a rapidly progressive subgroup of subjects with chronic heart failure and left ventricular systolic dysfunction who experience a high HF-MACE.

In subjects with baseline LVESV>70 ml, >80 ml, >90 ml, >100 ml, >110 ml or >120 ml, treatment with high dose (150 million) MPCs resulted in greater improvement in cardiac remodelling variables and HF-MACE than was seen in control subjects.

The findings presented herein identify an optimal target group for the cardioprotective benefits of cell therapy and facilitate improvement in trial design for subjects with heart failure due to left ventricular systolic dysfunction.

Control patients with advanced heart failure (baseline LVESV>100 ml) were the fastest progressors over 6 months in terms of significant worsening in LVESV and LVEDV volumes, and loss of LVEF. Over a 6 month follow-up period, the 150 million MPC dose had a substantial cardioprotective effect on LVESV (p<0.02), LVEDV (p<0.03) and LVEF (p<0.05) in Class I/III patients with substantial baseline LV contractile abnormality (i.e. those with baseline LVESV>100 ml).

Over a 6 month follow-up period, the 150 million MPC dose had a substantial cardioprotective effect on LVESV (p<0.02), LVEDV (p<0.03) and LVEF (p<0.05) in Class II/III patients with substantial baseline LV contractile abnormality (i.e. those with baseline LVESV>100 ml).

The invention claimed is:

1. A method for treating chronic heart failure due to left ventricular systolic dysfunction in a human subject characterized by:
   (i) a baseline left ventricular end systolic volume (LVESV) of greater than 100 mL; and
   (ii) a baseline left ventricular ejection fraction (LVEF) of less than or equal to about 35%;
   wherein the method comprises administering to the myocardium of the human subject's heart, a population of culture expanded STRO-1+ mesenchymal lineage precursor cells (MPCs), so as to decrease the human subject's baseline LVESV or decrease the human subject's baseline left ventricular end diastolic volume (LVEDV) by at least 8 mL 6 months after administration of the MPCs.

2. The method according to claim 1, wherein the MPCs have been culture expanded from a population of STRO-1+ and STRO-3+ cells.

3. The method of claim 1, wherein:
(i) the baseline LVESV is due to acute myocardial infarction; or
(ii) the baseline LVESV is due to chronic congestive heart failure.

4. The method according to claim 1, wherein the human subject has an LVESV of greater than 110 mL.

5. The method according to claim 1, wherein the population of MPCs is administered to the subject by a catheter-based system.

6. The method according to claim 5, wherein the population of MPCs is administered to the subject by transendocardial injection, intracoronary infusion, intravenous infusion or transepicardial injection.

7. The method according to claim 1 wherein the heart failure is due to hypertension, ischemic or non-ischemic cardiomyopathy, myocarditis, obesity, or diabetes.

8. The method according to claim 1, wherein the population of MPCs is administered to the subject between about 1 day and 7 days following a diagnosis of heart failure.

9. The method according to claim 1, comprising administering a population of culture expanded STRO-1$^+$ MPCs from $1\times10^6$ to $8\times10^8$ to the subject in a single dose or over multiple doses.

10. The method of claim 1, wherein the human subject is administered a population of culture expanded STRO-1$^+$ MPCs of about $1.50\times10^6$ MPCs.

11. The method according to claim 1, wherein the population of MPCs is administered to the subject in the form of a composition comprising a pharmaceutically acceptable carrier and/or excipient.

12. The method according to claim 1, wherein the population of MPCs is allogeneic.

13. The method according to claim 1, wherein the population of STRO-1$^+$ MPCs are STRO-1$^{bright}$ cells.

14. The method according to claim 1, wherein the population of MPCs is provided in a kit, together with a delivery device.

* * * * *